US008592196B2

(12) United States Patent
Kittel et al.

(10) Patent No.: US 8,592,196 B2
(45) Date of Patent: Nov. 26, 2013

(54) MODIFIED INFLUENZA VIRUS

(75) Inventors: Christian Kittel, Langenlois (AT); Nina Wressnigg, Vienna (AT)

(73) Assignee: Baxter Healthcare SA, Opfikon (CH)

( * ) Notice: Subject to any disclaimer, the term of this patent is extended or adjusted under 35 U.S.C. 154(b) by 447 days.

(21) Appl. No.: 12/809,814

(22) PCT Filed: Dec. 22, 2008

(86) PCT No.: PCT/EP2008/068154
§ 371 (c)(1), (2), (4) Date: Aug. 23, 2010

(87) PCT Pub. No.: WO2009/080806
PCT Pub. Date: Jul. 2, 2009

(65) Prior Publication Data

US 2010/0322970 A1 Dec. 23, 2010

(30) Foreign Application Priority Data

Dec. 21, 2007 (EP) .................................... 07450244

(51) Int. Cl.
*A61K 39/145* (2006.01)
*C07H 21/00* (2006.01)
*C12N 7/04* (2006.01)
*A61P 31/16* (2006.01)
*A61P 37/04* (2006.01)

(52) U.S. Cl.
USPC .................. 435/235.1; 424/209.1; 424/184.1; 424/93.1; 536/23.72; 435/236; 435/320.1

(58) Field of Classification Search
None
See application file for complete search history.

(56) References Cited

U.S. PATENT DOCUMENTS

| | | | | |
|---|---|---|---|---|
| 6,852,522 | B1 * | 2/2005 | Palese et al. | 435/239 |
| 8,097,459 | B2 * | 1/2012 | Jin et al. | 435/440 |
| 2007/0122430 | A1 * | 5/2007 | Shneider et al. | 424/204.1 |
| 2008/0175863 | A1 * | 7/2008 | Jin et al. | 424/209.1 |
| 2010/0136052 | A1 * | 6/2010 | Wolschek et al. | 424/206.1 |

FOREIGN PATENT DOCUMENTS

| | | |
|---|---|---|
| EP | 2 045 323 | 4/2009 |
| EP | 2 048 237 | 4/2009 |
| WO | WO 99/64068 | 12/1999 |
| WO | WO 99/64571 | 12/1999 |
| WO | WO 2006/119527 | 11/2006 |

OTHER PUBLICATIONS

Wressnigg N, Voss D, Wolff T, Romanova J, Ruthsatz T, Mayerhofer I, Reiter M, Nakowitsch S, Humer J, Morokutti A, Muster T, Egorov A, Kittel C. Development of a live-attenuated influenza B DeltaNS1 intranasal vaccine candidate. Vaccine. May 11, 2009;27(21):2851-7. Epub Mar. 11, 2009.*

Wressnigg, N. Influenza B NS1 Truncation Mutants: A Live Attenuated Vaccine Approach. Universitat Wien Doctoral Dissertation. Adv: Thomas Muster. Dec. 16, 2008.*

Wressnigg N, Shurygina AP, Wolff T, Redlberger-Fritz M, Popow-Kraupp T, Muster T, Egorov A, Kittel C. Influenza B mutant viruses with truncated NS1 proteins grow efficiently in Vero cells and are immunogenic in mice. J Gen Virol. Feb. 2009;90(Pt 2):366-74.*

Ferko B, Stasakova J, Romanova J, Kittel C, Sereinig S, Katinger H, Egorov A. Immunogenicity and protection efficacy of replication-deficient influenza A viruses with altered NS1 genes. J Virol. Dec. 2004;78(23):13037-45.*

McCullers JA, Hoffmann E, Huber VC, Nickerson AD. A single amino acid change in the C-terminal domain of the matrix protein M1 of influenza B virus confers mouse adaptation and virulence. Virology. Jun. 5, 2005;336(2):318-26.*

Hiebert SW, Williams MA, Lamb RA. Nucleotide sequence of RNA segment 7 of influenza B/Singapore/222/79: maintenance of a second large open reading frame. Virology. Dec. 1986;155(2):747-51.*

Aqeilan et al., "Mechanism of action of interleukin-2 (IL-2)-Bax, an apoptosis-inducing chimaeric protein targeted against cells expressing the IL-2 receptor," *Biochem. J.*, 370:129-140, 2003.

Caton and Brownies, "The antigenic structure of the influenza virus A/PR/8/34 hemagglutinin (H1 subtype)," *Cell*, 31:417-427, 1982.

Chen et al., "Genetic mapping of the cold-adapted phenotype of B/Ann Arbor/1/66, the master donor virus for live attenuated influenza vaccines (FluMist®)," *Virology*, 345:416-423, 2006.

Couch, "Advances in influenza virus vaccine research," In: *Immunomodulating Drugs*, 685:803-812, 1993.

Dauber et al., "Double-stranded RNA binding of influenza B virus nonstructural NS1 protein inhibits protein kinase B but is not essential to antagonize production of the alpha/beta interferon," *J. Virol.*, 80:11667-11677, 2006.

Dauber et al., "The influenza B virus nonstructural NS1 protein is essential for efficient viral growth and antagonizes beta interferon induction," *J. Virol.*, 78:1865-1872, 2004.

Hai et al., "Influenza B NS1 truncation mutant viruses: a live-attenuated vaccine approach," *J. Virol.*, pp. 10508-10590, Nov. 2008.

Hatta and Kawaoka, "The NB protein of influenza B virus is not necessary for virus replication in vitro," *J. Virol.*, 77:6050-4, 2003.

Hoffman et al., "A DNA transfection system for generation of influenza A virus from eight plasmids," *PNAS*, 97:6108-13, 2000.

Lamb and Horvath, "Diversity of coding strategies in influenza viruses," *Trens. Genet.*, 7:261-6, 1991.

Nemeroff et al., "Identification of cis-acting intron and exon regions in influenza virus NS1 mRNA that inhibit splicing and cause the formation of aberrantly sedimenting presplicing complexes," *Mol. Cell. Biol.*, 12:962-70, 1992.

Neumann and Kawaoka, "Genetic engineering of influenza and other negative-strand RNA viruses containing segmented genomes," *Advances in Virus Research*, 53:265-300, 1999.

(Continued)

*Primary Examiner* — Benjamin P Blumel
*Assistant Examiner* — Rachel Gill
(74) *Attorney, Agent, or Firm* — Fulbright & Jaworski LLP

(57) ABSTRACT

The present invention provides an influenza B virus M gene with a modification of at least one nucleotide proximate to the N-terminus of the M gene, more specifically at any one of nucleotide positions 265 to 294 of the M gene. The present invention also provides an influenza B virus comprising the modified M gene, the use of the modified M gene for the preparation of a vaccine and methods for preparing the modified influenza virus.

20 Claims, 18 Drawing Sheets

(56) References Cited

OTHER PUBLICATIONS

Figure 1A:
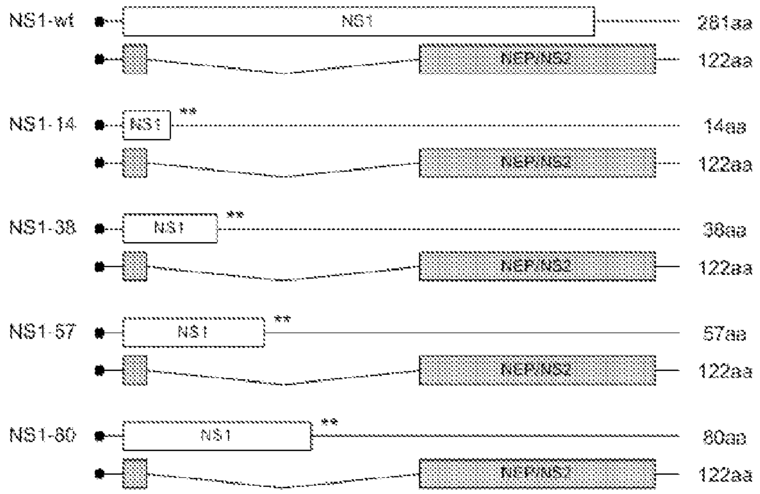

Pleschka et al., "A plasmid-based reverse genetics system for influenza A virus," *J. Virol.*, 70:4188-92, 1996.

Plotch and Krug, "In vitro splicing of influenza viral NS1 mRNA and NS1-β-globin chimeras: possible mechanisms for the control of viral mRNA splicing," *Proc. Natl. Acad. Sci. USA*, 83:5444-5448, 1986.

Spiro et al., "Influenza B virus (B/Florida/UR06-0006/2006) segment 7," Database EMBL, Accession No. CY022246, Jun. 19, 2007.

Spiro et al., "Influenza B virus (B/Nepal/1331/2005)" Database EMBL, Accession No. A3DQL7, Mar. 20, 2007.

Williams et al., "Immunization policies and vaccine coverage among adults," *Annuals of Internal Medicine*, 108:616-25, 1988.

* cited by examiner

Fig 5

| Virus strain | Accession number | Amino acid sequence |
|---|---|---|
| | | 61 86 115 |
| B/Malaysia/2506/04-adapted | | G A S I C F L K P K D Q E R K R R F I T E P L S G **V** G T T A T K K K G L I L A E R K M R R C V S F H E A F E I A |
| B/Malaysia/2506/04-swab | | . . . . . . . . . . . . . . . . . . . . . . . . . **M** . . . . . . . . . . . . . . . . . . . . . . . . . . . . . . |
| B/Lee/40 | ABG85182 | . . . . . . . . . . . . . . . . . . . . . . . . . **M** . . . . . . . . . . . . . . . . . . . . . . . . . . . . . . |
| B/Ann Arbor/1/1966 | AAA66414 | . . . . . . . . . . . . . . . . . . . . . . . . . **M** . . . . . . . . . . . . . . . . . . . . . . . . . . . . . . |
| B/Victoria/2/87 | ABL77245 | . . . . . . . . . . . . . . . . . . . . . . . . . **M** . . . . . . . . . . . . . . . . . . . . . . . . . . . . . . |
| B/Yamagata/16/88 | ABL77256 | . . . . . . . . . . . . . . . . . . . . . . . . . **M** . . . . . . . . . . . . . . . . . . . . . . . . . . . . . . |
| B/Beijing/184/93 | CAH03806 | . . . . . . . . . . . . . . . . . . . . . . . . . **M** . . . . . . . . . . . . . . . . . . . . . . . . . . . . . . |
| B/Shandong/7/97 | AAK95902 | . . . . . . . . . . . . . . . . . . . . . . . . . **M** . . . . . . . . . . . . . . . . . . . . . . . . . . . . . . |
| B/Sichuan/379/99 | CAH03800 | . . . . . . . . . . . . . . . . . . . . . . . . . **M** . . . . . . . . . . . . . . . . . . . . . . . . . . . . . . |
| B/Hong Kong/330/2001 | AAT69440 | . . . . . . . . . . . . . . . . . . . . . . . . . **M** . . . . . . . . . . . . . . . . . . . . . . . . . . . . . . |
| B/Hong Kong/1434/2002 | ABL77146 | . . . . . . . . . . . . . . . . . . . . . . . . . **M** . . . . . . . . . . . . . . . . . . . . . . . . . . . . . . |
| B/Jiangsu/10/2003 | ACF54203 | . . . . . . . . . . . . . . . . . . . . . . . . . **M** . . . . . . . . . . . . . . . . . . . . . . . . . . . . . . |
| B/Florida/04/2006 | ACF54247 | . . . . . . . . . . . . . . . . . . . . . . . . . **M** . . . . . . . . . . . . . . . . . . . . . . . . . . . . . . |

Fig 7a

MSLFGDTIAYLLSLTEDGEGKAELAEKLHCWFGGKEFDLDSALEWIKNKRCLTDIQKALI
GASICFLKPKDQERKRRFITEPLSGVGTTATKKKGLILAERKMRRCVSFHEAFEIAEGHE
SSALLYCLMVMYLNPGNYSMQVKLGTLCALCEKQASHSHRAHSRAARSSVPGVRREM
QMVSAMNTAKTMNGMGKGEDVQKLAEELQSNIGVLRSLGASQKNGEGIAKDVMEVLK
QSSMGNSALVKKYL. (SEQ ID. No 1)

Fig 7b

MSLFGDTIAYLLSLTEDGEGKAELAEKLHCWFGGKEFDLDSALEWIKNKRCLTDIQKALI
GASICFLKPKDQERKRRFITEPLSGVGTTATKKKGLILAERKMRKCVSFHEAFEIAEGHE
SSALLYCLMVMYLNPGNYSMQVKLGTLCALCEKQASHSHRAHSRAARSSVPGVRREM
QMVSAMNTAKTMNGMGKGEDVQKLAEELQSNIGVLRSLGASQKNGEGIAKDVMEVLK
QSSMGNSALVKKYL (SEQ ID. No 2)

Fig 8a

| Virus | Backbone | Surface glycoproteins HA and HA | M | NS |
|---|---|---|---|---|
| Thür-ΔNS1-14 M1-M86V+C950T 6:2 | B/Vienna/33/06 | B/Thüringen/02/06 | M1-M86V +C950T | ΔNS1-14 |
| Thür-ΔNS1-38 M1-M86V 6:2 | B/Vienna/33/06 | B/Thüringen/02/06 | M1-M86V | ΔNS1-38 |
| Thür-ΔNS1-38 M1-M86V+C950T 6:2 | B/Vienna/33/06 | B/Thüringen/02/06 | M1-M86V +C950T | ΔNS1-38 |
| Thür-ΔNS1-57 M1-M86V+C950T 6:2 | B/Vienna/33/06 | B/Thüringen/02/06 | M1-M86V +C950T | ΔNS1-57 |
| Thür-ΔNS1-64 M1-M86V+C950T 6:2 | B/Vienna/33/06 | B/Thüringen/02/06 | M1-M86V +C950T | ΔNS1-64 |
| Thür-ΔNS1-80 M1-wt 6:2 | B/Vienna/33/06 | B/Thüringen/02/06 | M1-wt | ΔNS1-80 |
| Thür-ΔNS1-80 M1-M86V 6:2 | B/Vienna/33/06 | B/Thüringen/02/06 | M1-M86V | ΔNS1-80 |
| Thür-ΔNS1-80 M1-C950T 6:2 | B/Vienna/33/06 | B/Thüringen/02/06 | M1-C950T | ΔNS1-80 |
| Thür-ΔNS1-80 M1-M86V+C950T 6:2 | B/Vienna/33/06 | B/Thüringen/02/06 | M1-M86V +C950T | ΔNS1-80 |
| Thür-NS1wt M1-wt 6:2 | B/Vienna/33/06 | B/Thüringen/02/06 | M1-wt | NS1 wt |
| Thür-NS1wt M1-M86V 6:2 | B/Vienna/33/06 | B/Thüringen/02/06 | M1-M86V | NS1 wt |
| Thür-NS1-wt M1-C950T 6:2 | B/Vienna/33/06 | B/Thüringen/02/06 | M1-C950T | NS1- wt |
| Thür-NS1-wt M1-M86V+C950T 6:2 | B/Vienna/33/06 | B/Thüringen/02/06 | M1-M86V +C950T | NS1- wt |
| Florida_NS1-38 M1wt | B/Thüringen/02/06 | B/Florida/04/06 | M1-wt | NS1-38 |
| B/Florida_NS1-80 M1wt | B/Thüringen/02/06 | B/Florida/04/06 | M1-wt | NS1-80 |
| B/Florida_NS1-wt M1wt | B/Thüringen/02/06 | B/Florida/04/06 | M1-wt | NS1-wt |
| B/Florida_delNS M1 M86V | B/Thüringen/02/06 | B/Florida/04/06 | M1-M86V | ΔNS1 |
| B/Florida_NS1-38 M1M86V | B/Thüringen/02/06 | B/Florida/04/06 | M1-M86V | NS1-38 |
| B/Florida_NS1-80 M1M86V | B/Thüringen/02/06 | B/Florida/04/06 | M1-M86V | NS1-80 |
| B/Florida_NS1-wt M1M86V | B/Thüringen/02/06 | B/Florida/04/06 | M1-M86V | NS1-wt |

Fig 8b

AGCAGAAGCACGCACTTTCTTAAAatgtcgctgtttggagacacaattgcctacctgctttcattgacagaag
atggagaaggcaaagcagaactagcagaaaaattacactgttggtttggtgggaaagaatttgacctagactctgccttgg
aatggataaaaaacaaaagatgcttaactgatatacaaaaagcactaattggtgcctctatatgctttttaaaacccaaaga
ccaggaaagaaaaagaagattcatcacagagcccttatcaggaGtgggaacaacagcaacaaaaaagaaaggcct
gattctggctgagagaaaaatgagaagatgtgtgagctttcatgaagcatttgaaatagcagaaggccatgaaagctcag
cgctactatactgtctcatggtcatgtacctgaatcctggaaattattcaatgcaagtaaaactaggaacgctctgtgctttatg
cgagaaacaagcatcacattcacacagggctcatagcagagcagcgagatcttcagtgcctggagtgagacgagaaat
gcagatggtctcagctatgaacacagcaaaaacaatgaatggaatgggaaaaggagaagacgtccaaaagttggcag
aagagctgcaaagcaacattggagtgctgagatctcttggggcaagtcaaaagaatggggaagggattgcaaaggatg
taatggaagtgctaaagcagagctccatgggaaattcagctcttgtgaagaaatatctataatgctcgaaccatttcagattc
tttcaatttgttcttttatcttatcagctctccatttcatggcttggacaatagggcatttgaatcaaataaaaagaggaataaaca
tgaaaatacgaataaaaggtccaaacaaagagacaataaacagagaggtatcaattttgagacacagttaccaaaaag
aaatccaggccaaagaaacaatgaaggaagtactctctgacaacatggaggtattgagtgaccacataataattgaggg
gctttctgccgaagagataataaaaatgggtgaaacagttttggagatagaagaattgcattaaATTCAATTTTACT
GTATTTCTTACTATGCATTTAAGCAAATTGTAATCAATGTCAGCAAATAAACTGGAAA
AAGTGCGTTGTTTCTACT (SEQ ID. No 3)

Fig 8c

AGCAGAAGCACGCACTTTCTTAAAatgtcgctgtttggagacacaattgcctacctgctttcattgacagaag
atggagaaggcaaagcagaactagcagaaaaattacactgttggtttggtgggaaagaatttgacctagactctgccttgg
aatggataaaaaacaaaagatgcttaactgatatacaaaaagcactaattggtgcctctatatgctttttaaaacccaaaga
ccaggaaagaaaaagaagattcatcacagagcccttatcaggaGtgggaacaacagcaacaaaaaagaaaggcct
gattctggctgagagaaaaatgagaagatgtgtgagctttcatgaagcatttgaaatagcagaaggccatgaaagctcag
cgctactatactgtctcatggtcatgtacctgaatcctggaaattattcaatgcaagtaaaactaggaacgctctgtgctttatg
cgagaaacaagcatcacattcacacagggctcatagcagagcagcgagatcttcagtgcctggagtgagacgagaaat
gcagatggtctcagctatgaacacagcaaaaacaatgaatggaatgggaaaaggagaagacgtccaaaagttggcag
aagagctgcaaagcaacattggagtgctgagatctcttggggcaagtcaaaagaatggggaagggattgcaaaggatg
taatggaagtgctaaagcagagctccatgggaaattcagctcttgtgaagaaatatctataatgctcgaaccatttcagattc
tttcaatttgttcttttatcttatcagctctccatttcatggcttggacaatagggcatttgaatcaaataaaaagaggaataaaca
tgaaaatacgaataaaaggtccaaacaaagagacaataaacagagaggtatcaattttgagacacagttaTcaaaaa
gaaatccaggccaaagaaacaatgaaggaagtactctctgacaacatggaggtattgagtgaccacataataattgagg
ggctttctgccgaagagataataaaaatgggtgaaacagttttggagatagaagaattgcattaaATTCAATTTTAC
TGTATTTCTTACTATGCATTTAAGCAAATTGTAATCAATGTCAGCAAATAAACTGGAA
AAAGTGCGTTGTTTCTACT (SEQ ID No. 4)

Fig 8d

AGCAGAAGCACGCACTTTCTTAAAATGTCGCTGTTTGGAGACACAATTGCCTACCT
GCTTTCATTGACAGAAGATGGAGAAGGCAAAGCAGAACTAGCAGAAAAATTACACT
GTTGGTTCGGTGGGAAAGAATTTGACCTAGACTCTGCCTTGGAATGGATAAAAAAC
AAAAGATGCTTAACTGATATACAGAAAGCACTAATTGGTGCCTCTATCTGCTTTTTAA
AACCCAAAGACCAGGAAAGAAAAAGAAGATTCATCACAGAGCCCCTATCAGGAATG
GGAACAACAGCAACAAAAAAGAAGGGCCTGATTCTAGCTGAGAGAAAAATGAGAAA
ATGTGTGAGCTTCCATGAAGCATTTGAAATAGCAGAAGGCCATGAAAGCTCAGCGT
TACTATATTGTCTCATGGTCATGTACCTGAATCCTGGAAATTATTCAATGCAAGTAAA
ACTAGGAACGCTCTGTGCTTTGTGCGAAAAACAAGCATCACATTCACACAGGGCTC
ATAGCAGAGCAGCGAGATCTTCAGTGCCCGGAGTGAGACGGGAAATGCAGATGGT
CTCAGCTATGAACACAGCAAAAACAATGAATGGAATGGGAAAAGGAGAAGACGTCC
AAAAACTGGCAGAAGAACTGCAAAGCAACATTGGAGTATTGAGATCTCTTGGGGCA
AGTCAAAAGAATGGGGAAGGAATTGCAAAGGATGTAATGGAAGTGCTAAAGCAGAG
CTCTATGGGAAATTCAGCTCTTGTGAAGAAATACCTATAATGCTCGAACCATTTCAG
ATTCTTTCAATTTGTTCTTTTATTTTATCAGCTCTCCATTTCATGGCTTGGACAATAG
GACATTTAAATCAAATAAAAAGAGGAGTAAACATGAAAATACGAATAAAGGGGCCAA
ATAAAGAGACAATAAACAGAGAGGTATCAATTTTGAGACACAGTTACCAAAAAGAAA
TCCAGGCTAAAGAAGCAATGAAGGAAGTACTCTCTGACAACATGGAGGTATTGAGT
GACCACATAGTAATTGAGGGGCTTTCTGCTGAAGAGATAATAAAAATGGGTGAAAC
AGTTTTGGAGGTAGAAGAATTTCATTAAATTCAATTTTTACTGTACTTCTTACTATGC
ATTTAAGCAAATTGTAATCAATGTCAGCAAATAAACTGGAAAAAGTGCGTTGTTTCTA
CT (SEQ ID No. 5)

Fig 8e

AGCAGAAGCACGCACTTTCTTAAAATGTCGCTGTTTGGAGACACAATTGCCTACCT
GCTTTCATTGACAGAAGATGGAGAAGGCAAAGCAGAACTAGCAGAAAAATTACACT
GTTGGTTCGGTGGGAAAGAATTTGACCTAGACTCTGCCTTGGAATGGATAAAAAAC
AAAAGATGCTTAACTGATATACAGAAAGCACTAATTGGTGCCTCTATCTGCTTTTTAA
AACCCAAAGACCAGGAAAGAAAAAGAAGATTCATCACAGAGCCCCTATCAGGAgTG
GGAACAACAGCAACAAAAAAGAAGGGCCTGATTCTAGCTGAGAGAAAAATGAGAAA
ATGTGTGAGCTTCCATGAAGCATTTGAAATAGCAGAAGGCCATGAAAGCTCAGCGT
TACTATATTGTCTCATGGTCATGTACCTGAATCCTGGAAATTATTCAATGCAAGTAAA
ACTAGGAACGCTCTGTGCTTTGTGCGAAAAACAAGCATCACATTCACACAGGGCTC
ATAGCAGAGCAGCGAGATCTTCAGTGCCCGGAGTGAGACGGGAAATGCAGATGGT
CTCAGCTATGAACACAGCAAAAACAATGAATGGAATGGGAAAAGGAGAAGACGTCC
AAAAACTGGCAGAAGAACTGCAAAGCAACATTGGAGTATTGAGATCTCTTGGGGCA
AGTCAAAAGAATGGGGAAGGAATTGCAAAGGATGTAATGGAAGTGCTAAAGCAGAG
CTCTATGGGAAATTCAGCTCTTGTGAAGAAATACCTATAATGCTCGAACCATTTCAG
ATTCTTTCAATTTGTTCTTTTATTTTATCAGCTCTCCATTTCATGGCTTGGACAATAG
GACATTTAAATCAAATAAAAAGAGGAGTAAACATGAAAATACGAATAAAGGGGCCAA
ATAAAGAGACAATAAACAGAGAGGTATCAATTTTGAGACACAGTTACCAAAAAGAAA
TCCAGGCTAAAGAAGCAATGAAGGAAGTACTCTCTGACAACATGGAGGTATTGAGT
GACCACATAGTAATTGAGGGGCTTTCTGCTGAAGAGATAATAAAAATGGGTGAAAC
AGTTTTGGAGGTAGAAGAATTTCATTAAATTCAATTTTTACTGTACTTCTTACTATGC
ATTTAAGCAAATTGTAATCAATGTCAGCAAATAAACTGGAAAAAGTGCGTTGTTTCTA
CT (SEQ ID No. 6)

Fig 8 f

AGCAGAAGCACGCACTTTCTTAAAatgtcgctgtttggagacacaattgcctacctgctttcattgacagaag
atggagaaggcaaagcagaactagcagaaaaattacactgttggtttggtgggaaagaatttgacctagactctgccttgg
aatggataaaaaacaaaagatgcttaactgatatacaaaaagcactaattggtgcctctatatgctttttaaaacccaaaga
ccaggaaagaaaaagaagattcatcacagagcccttatcaggaatgggaacaacagcaacaaaaaagaaaggcct
gattctggctgagagaaaaatgagaagatgtgtgagctttcatgaagcatttgaaatagcagaaggccatgaaagctcag
cgctactatactgtctcatggtcatgtacctgaatcctggaaattattcaatgcaagtaaaactaggaacgctctgtgctttatg
cgagaaacaagcatcacattcacacagggctcatagcagagcagcgagatcttcagtgcctggagtgagacgagaaat
gcagatggtctcagctatgaacacagcaaaaacaatgaatggaatgggaaaaggagaagacgtccaaaagttggcag
aagagctgcaaagcaacattggagtgctgagatctcttggggcaagtcaaaagaatggggaagggattgcaaaggatg
taatggaagtgctaaagcagagctccatgggaaattcagctcttgtgaagaaatatctataatgctcgaaccatttcagattc
tttcaatttgttcttttatcttatcagctctccatttcatggcttggacaatagggcatttgaatcaaataaaaagaggaataaaca
tgaaaatacgaataaaaggtccaaacaaagagacaataaacagagaggtatcaattttgagacacagttaTcaaaaa
gaaatccaggccaaagaaacaatgaaggaagtactctctgacaacatggaggtattgagtgaccacataataattgagg
ggctttctgccgaagagataataaaaatgggtgaaacagttttggagatagaagaattgcattaaATTCAATTTTAC
TGTATTTCTTACTATGCATTTAAGCAAATTGTAATCAATGTCAGCAAATAAACTGGAA
AAAGTGCGTTGTTTCTACT (SEQ ID No. 7)

Fig 8g agcagaagcagaggatttgtttagtcactggcaaacaggaaaaaATGGCGAACAACATGACCACAACA
CAAATTGAGGTGGGTCCGtgatgaCCCAATGGATACAAGTCCTTATCAACTCTGCATA
GATTGAATGCATATGACCAGAGTGGAAGGCTTGTTGCTAAACTTGTTGCCACTGAT
GATCTTACAGTGGAGGATGAAGAAGATGGCCATCGGATCCTCAACTCACTCTTCGA
GCGTCTTAATGAAGGACATTCAAAGCCAATTCGAGCAGCTGAAACTGCGGTGGGA
GTCTTATCCCAATTTGGTCAAGAGCACCGATTATCACCAGAAGAGGGAGACAATTA
GACTGGTCACGGAAGAACTTTATCTTTTAAGTAAAAGAATTGATGATAACATATTATT
CCACAAAACAGTAATAGCTAACAGCTCCATAATAGCTGACATGGTTGTATCATTATC
ATTATTAGAAACATTGTATGAAATGAAGGATGTGGTTGAAGTGTACAGCAGGCAGT
GCTTGTGAatttaaaataaaaatcctcttgttactact (SEQ ID No. 8)

Fig 8h agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAtgatgaCCCAATGGATACAAGTCC
TTATCAACTCTGCATAGATTGAATGCATATGACCAGAGTGGAAGGCTTGTTGCTAAA
CTTGTTGCCACTGATGATCTTACAGTGGAGGATGAAGAAGATGGCCATCGGATCCT
CAACTCACTCTTCGAGCGTCTTAATGAAGGACATTCAAAGCCAATTCGAGCAGCTG
AAACTGCGGTGGGAGTCTTATCCCAATTTGGTCAAGAGCACCGATTATCACCAGAA
GAGGGAGACAATTAGACTGGTCACGGAAGAACTTTATCTTTTAAGTAAAAGAATTGA
TGATAACATATTATTCCACAAAACAGTAATAGCTAACAGCTCCATAATAGCTGACAT
GGTTGTATCATTATCATTATTAGAAACATTGTATGAAATGAAGGATGTGGTTGAAGT
GTACAGCAGGCAGTGCTTGTGAatttaaaataaaaatcctcttgttactact (SEQ ID No. 9)

Fig 8i agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAGCCCTTGACTACCCTGGTCAAG
ACCGCCTAAACAGACTAAAGAGAAAATTAGAGTCAtgatgaCCCAATGGATACAAGTC
CTTATCAACTCTGCATAGATTGAATGCATATGACCAGAGTGGAAGGCTTGTTGCTAA
ACTTGTTGCCACTGATGATCTTACAGTGGAGGATGAAGAAGATGGCCATCGGATCC
TCAACTCACTCTTCGAGCGTCTTAATGAAGGACATTCAAAGCCAATTCGAGCAGCT
GAAACTGCGGTGGGAGTCTTATCCCAATTTGGTCAAGAGCACCGATTATCACCAGA
AGAGGGAGACAATTAGACTGGTCACGGAAGAACTTTATCTTTTAAGTAAAAGAATTG
ATGATAACATATTATTCCACAAAACAGTAATAGCTAACAGCTCCATAATAGCTGACAT
GGTTGTATCATTATCATTATTAGAAACATTGTATGAAATGAAGGATGTGGTTGAAGT
GTACAGCAGGCAGTGCTTGTGAatttaaaataaaaatcctcttgttactact (SEQ ID No. 10)

Fig 8j agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAGCCCTTGACTACCCTGGTCAAG
ACCGCCTAAACAGACTAAAGAGAAAATTAGAGTCAAGAATAAAGACTCACAACAAAt
gatgaCCCAATGGATACAAGTCCTTATCAACTCTGCATAGATTGAATGCATATGACCA
GAGTGGAAGGCTTGTTGCTAAACTTGTTGCCACTGATGATCTTACAGTGGAGGATG
AAGAAGATGGCCATCGGATCCTCAACTCACTCTTCGAGCGTCTTAATGAAGGACAT
TCAAAGCCAATTCGAGCAGCTGAAACTGCGGTGGGAGTCTTATCCCAATTTGGTCA
AGAGCACCGATTATCACCAGAAGAGGGAGACAATTAGACTGGTCACGGAAGAACTT
TATCTTTTAAGTAAAAGAATTGATGATAACATATTATTCCACAAAACAGTAATAGCTA
ACAGCTCCATAATAGCTGACATGGTTGTATCATTATCATTATTAGAAACATTGTATGA
AATGAAGGATGTGGTTGAAGTGTACAGCAGGCAGTGCTTGTGAatttaaaataaaaatcctct
tgttactact (SEQ ID No. 11)

Fig 8k agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAGCCCTTGACTACCCTGGTCAAG
ACCGCCTAAACAGACTAAAGAGAAAATTAGAGTCAAGAATAAAGACTCACAACAAAA
GTGAGCCTGAAAGTAAAAGGATGTCCCTTGAAGAGAGAAAAGCAATTtgatgaCCCAA
TGGATACAAGTCCTTATCAACTCTGCATAGATTGAATGCATATGACCAGAGTGGAAG
GCTTGTTGCTAAACTTGTTGCCACTGATGATCTTACAGTGGAGGATGAAGAAGATG
GCCATCGGATCCTCAACTCACTCTTCGAGCGTCTTAATGAAGGACATTCAAAGCCA
ATTCGAGCAGCTGAAACTGCGGTGGGAGTCTTATCCCAATTTGGTCAAGAGCACCG
ATTATCACCAGAAGAGGGAGACAATTAGACTGGTCACGGAAGAACTTTATCTTTTAA
GTAAAAGAATTGATGATAACATATTATTCCACAAAACAGTAATAGCTAACAGCTCCAT
AATAGCTGACATGGTTGTATCATTATCATTATTAGAAACATTGTATGAAATGAAGGAT
GTGGTTGAAGTGTACAGCAGGCAGTGCTTGTGAatttaaaataaaaatcctcttgttactact (SEQ ID No. 12)

Fig 8l

AGCAGAAGCAGAGGATTTGTTTAGTCACTGGCAAACAGGAAAAAATGGCGAACAAC
ATGACCACAACACAAATTGAGTGGAGGATGAAGAAGATGGCCATCGGATCCTCAAC
TCACTCTTCGAGCGTCTTAATGAAGGACATTCAAAGCCAATTCGAGCAGCTGAAAC
TGCGGTGGGAGTCTTATCCCAATTTGGTCAAGAGCACCGATTATCACCAGAAGAGG
GAGACAATtagACTGGTCACGGAAGAACTTTATCTTTTAAGTAAAAGAATTGATGATA
ACATATTATTCCACAAAACAGTAATAGCTAACAGCTCCATAATAGCTGACATGGTTG
TATCATTATCATTATTAGAAACATTGTATGAAATGAAGGATGTGGTTGAAGTGTACA
GCAGGCAGTGCTTGTGAATTTAAAATAAAAATCCTCTTGTTACTACT (SEQ ID No. 13)

Fig 8m

AGCAGAAGCAGAGGATTTGTTTAGTCACTGGCAAACAGGAAAAATGGCGGACAATA
TGACCACAACACAAATTGAGTGGAGGATGAAGAAGATGGCCATCGGATCCTCAATT
CACTCTTCGAGCGTCTTAATGAAGGACATTCAAAGCCAATTCGAGCAGCTGAAACT
GCGGTGGGAGTCTTATCCCAATTTGGTCAAGAGCACCGATTATCACCAGAAGAGG
GAGACAATTAGACTGGTCACGGAAGAACTTTATCTTTTAAGTAAAAGAATTGATGAT
AACATATTGTTCCACAAAACAGTAATAGCTAACAGCTCCATAATAGCTGACATGGTT
GTATCATTATCATTATTAGAAACATTGTATGAAATGAAGGATGTGGTTGAAGTGTAC
AGCAGGCAGTGCTTGTGAATTTAAAATAAAAATCCTCTTGTTACTACT (SEQ ID No. 14)

| Virus | Backbone | Surface glycoproteins HA and HA | M | NS |
|---|---|---|---|---|
| Thür-NS1-38StSt-IL2 M1-M86V+C950T 6:2 | B/Vienna/33/06 | B/Thüringen/02/06 | M1-M86V +C950T | NS1-38StSt-IL2 |
| Thür-NS1-80StSt-IL2 M1-M86V+C950T 6:2 | B/Vienna/33/06 | B/Thüringen/02/06 | M1-M86V +C950T | NS1-80StSt-IL2 |
| Thür-NS1-104StSt-IL2 M1-M86V+C950T 6:2 | B/Vienna/33/06 | B/Thüringen/02/06 | M1-M86V +C950T | NS1-104StSt-IL2 |
| Thür-NS1-145StSt-IL2 M1-M86V+C950T 6:2 | B/Vienna/33/06 | B/Thüringen/02/06 | M1-M86V +C950T | NS1-145StSt-IL2 |

Fig 9c agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAtaatgtacaggatgcaactcctgtcttgcattgc
actaagtcttgcacttgtcacaaacagtgcacctacttcttcgtcgacaaagaaaacacagctacaactggagcatttactg
ctggatttacagatgattttgaatggaattaataattacaagaatcccaaactcaccaggatgctcacatttaagttttacatgc
ccaagaaggccacagaactgaaacatcttcagtgtctagaagaagaactcaaacctctggaggaagtgctaaatttagct
caaagcaaaaactttcacttaagacccagggacttaatcagcaatatcaacgtaatagttctggaactaaagggatctgaa
acaacattcatgtgtgaatatgctgatgagacagcaaccattgtagaatttctgaacagatggattaccttttgtcaaagcatc
atctcaacactaacttgataaTACTAACCTTCTTCTCTTTCTTCTCCTGACAGtggAGGATGAAG
AAGATGGCCATCGGATCCTCAACTCACTCTTCGAGCGTCTTAATGAAGGACATTCA
AAGCCAATTCGAGCAGCTGAAACTGCGGTGGGAGTCTTATCCCAATTTGGTCAAGA
GCACCGATTATCACCAGAAGAGGGAGACAATTAGACTGGTCACGGAAGAACTTTAT
CTTTTAAGTAAAAGAATTGATGATAACATATTATTCCACAAAACAGTAATAGCTAACA
GCTCCATAATAGCTGACATGGTTGTATCATTATCATTATTAGAAACATTGTATGAAAT
GAAGGATGTGGTTGAAGTGTACAGCAGGCAGTGCTTGTGAatttaaaataaaaatcctcttgtta
ctact (SEQ ID No. 15)

Fig 9d agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAGCCCTTGACTACCCTGGTCAAG
ACCGCCTAAACAGACTAAAGAGAAAATTAGAGTCAAGAATAAAGACTCACAACAAAA
GTGAGCCTGAAAGTAAAAGGATGTCCCTTGAAGAGAGAAAAGCAATTtaatgtacaggat
gcaactcctgtcttgcattgcactaagtcttgcacttgtcacaaacagtgcacctacttcttcgtcgacaaagaaaacacagc
tacaactggagcatttactgctggatttacagatgattttgaatggaattaataattacaagaatcccaaactcaccaggatg
ctcacatttaagttttacatgcccaagaaggccacagaactgaaacatcttcagtgtctagaagaagaactcaaacctctg
gaggaagtgctaaatttagctcaaagcaaaaactttcacttaagacccagggacttaatcagcaatatcaacgtaatagttc
tggaactaaagggatctgaaacaacattcatgtgtgaatatgctgatgagacagcaaccattgtagaatttctgaacagatg
gattaccttttgtcaaagcatcatctcaacactaacttgataaTACTAACCTTCTTCTCTTTCTTCTCCTGA
CAGtggAGGATGAAGAAGATGGCCATCGGATCCTCAACTCACTCTTCGAGCGTCTTA
ATGAAGGACATTCAAAGCCAATTCGAGCAGCTGAAACTGCGGTGGGAGTCTTATCC
CAATTTGGTCAAGAGCACCGATTATCACCAGAAGAGGGAGACAATTAGACTGGTCA
CGGAAGAACTTTATCTTTTAAGTAAAAGAATTGATGATAACATATTATTCCACAAAAC
AGTAATAGCTAACAGCTCCATAATAGCTGACATGGTTGTATCATTATCATTATTAGAA
ACATTGTATGAAATGAAGGATGTGGTTGAAGTGTACAGCAGGCAGTGCTTGTGAattt
aaaataaaaatcctcttgttactact (SEQ ID No. 16)

Fig 9e agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAGCCCTTGACTACCCTGGTCAAG
ACCGCCTAAACAGACTAAAGAGAAAATTAGAGTCAAGAATAAAGACTCACAACAAAA
GTGAGCCTGAAAGTAAAAGGATGTCCCTTGAAGAGAGAAAAGCAATTGGAGTAAAA
ATGATGAAAGTACTCCTATTTATGAATCCGTCTGCTGGAATTGAAGGGTTTGAGCCA
TACTGTtaatgtacaggatgcaactcctgtcttgcattgcactaagtcttgcacttgtcacaaacagtgcacctacttcttcg
tcgacaaagaaaacacagctacaactggagcatttactgctggatttacagatgattttgaatggaattaataattacaaga
atcccaaactcaccaggatgctcacatttaagttttacatgcccaagaaggccacagaactgaaacatcttcagtgtctaga
agaagaactcaaacctctggaggaagtgctaaatttagctcaaagcaaaaactttcacttaagacccagggacttaatca
gcaatatcaacgtaatagttctggaactaaagggatctgaaacaacattcatgtgtgaatatgctgatgagacagcaacca
ttgtagaatttctgaacagatggattaccttttgtcaaagcatcatctcaacactaacttgataaTACTAACCTTCTTC
TCTTTCTTCTCCTGACAGtggAGGATGAAGAAGATGGCCATCGGATCCTCAACTCAC
TCTTCGAGCGTCTTAATGAAGGACATTCAAAGCCAATTCGAGCAGCTGAAACTGCG
GTGGGAGTCTTATCCCAATTTGGTCAAGAGCACCGATTATCACCAGAAGAGGGAGA
CAATTAGACTGGTCACGGAAGAACTTTATCTTTTAAGTAAAAGAATTGATGATAACAT
ATTATTCCACAAAACAGTAATAGCTAACAGCTCCATAATAGCTGACATGGTTGTATC
ATTATCATTATTAGAAACATTGTATGAAATGAAGGATGTGGTTGAAGTGTACAGCAG
GCAGTGCTTGTGAatttaaaataaaaatcctcttgttactact (SEQ ID No. 17)

Fig 9f agcagaagcagaggatttgtttagtcactggcaaacaggaaaaaATGGCGAACAACATGACCACAACA
CAAATTGAGGTGGGTCCGGGAGCAACCAATGCCACCATAAACTTTGAAGCAGGAAT
TCTGGAGTGCTATGAAAGGCTTTCATGGCAAAGAGCCCTTGACTACCCTGGTCAAG
ACCGCCTAAACAGACTAAAGAGAAAATTAGAGTCAAGAATAAAGACTCACAACAAAA
GTGAGCCTGAAAGTAAAAGGATGTCCCTTGAAGAGAGAAAAGCAATTGGAGTAAAA
ATGATGAAAGTACTCCTATTTATGAATCCGTCTGCTGGAATTGAAGGGTTTGAGCCA
TACTGTATGAAAAGTTCCTCAAATAGCAACTGTACGAAATACAATTGGACCGATTAC
CCTTCAACACCAGGGAGGTGCCTTGATGACATAGAAGAAGAACCAGAGGATGTTGA
TGGCCCAACTGAAATAtaatgtacaggatgcaactcctgtcttgcattgcactaagtcttgcacttgtcacaaacag
tgcacctacttcttcgtcgacaaagaaaacacagctacaactggagcatttactgctggatttacagatgattttgaatggaat
taataattacaagaatcccaaactcaccaggatgctcacatttaagttttacatgcccaagaaggccacagaactgaaac
atcttcagtgtctagaagaagaactcaaacctctggaggaagtgctaaatttagctcaaagcaaaaactttcacttaagacc
cagggacttaatcagcaatatcaacgtaatagttctggaactaaagggatctgaaacaacattcatgtgtgaatatgctgat
gagacagcaaccattgtagaatttctgaacagatggattaccttttgtcaaagcatcatctcaacactaacttgataaTACT
AACCTTCTTCTCTTTCTTCTCCTGACAGtggAGGATGAAGAAGATGGCCATCGGATC
CTCAACTCACTCTTCGAGCGTCTTAATGAAGGACATTCAAAGCCAATTCGAGCAGC
TGAAACTGCGGTGGGAGTCTTATCCCAATTTGGTCAAGAGCACCGATTATCACCAG
AAGAGGGAGACAATTAGACTGGTCACGGAAGAACTTTATCTTTTAAGTAAAAGAATT
GATGATAACATATTATTCCACAAAACAGTAATAGCTAACAGCTCCATAATAGCTGAC
ATGGTTGTATCATTATCATTATTAGAAACATTGTATGAAATGAAGGATGTGGTTGAA
GTGTACAGCAGGCAGTGCTTGTGAatttaaaataaaaatcctcttgttactact(SEQ ID No. 18)

MODIFIED INFLUENZA VIRUS

This application is a national phase application under 35 U.S.C. §371 of International Application No. PCT/EP2008/068154 filed 22 Dec. 2008, which claims priority to European Application No. 07450244.4 filed 21 Dec. 2007. The entire text of each of the above-referenced disclosures is specifically incorporated herein by reference.

The present invention covers an influenza B virus M gene comprising a modification of at least one nucleotide proximate to the N-terminus of the M gene, more specifically at any one of nucleotide positions 265 to 294 of the M gene as well as an influenza B virus comprising said modified M gene.

BACKGROUND OF THE INVENTION

Epidemics and pandemics caused by viral diseases are still claiming human lives and are impacting global economy. Influenza is responsible for millions of lost work days and visits to the doctor, hundreds of thousands of hospitalizations worldwide (Couch 1993, Ann. NY. Acad. Sci 685; 803,), tens of thousands of excess deaths (Collins & Lehmann 1953 Public Health Monographs 213:1; Glezen 1982 Am. J. Public Health 77:712) and billions of Euros in terms of health-care costs (Williams et al. 1988, Ann. Intern. Med. 108:616). Both influenza A and B viruses have in the past been responsible for these epidemics in humans, thus besides influenza A also influenza B virus surface antigens are an essential component of any vaccine effective in reducing influenza morbidity. Influenza viruses belong to the Orthomyxoviridae family and are characterized by segmental negative-strand RNA genomes that add up to total sizes of 13.6 to 14.6 kb, respectively. Genomic viral RNA must be packaged into viral particles in order for the virus to be transmitted. The process by which progeny viral particles are assembled and the protein/protein interactions occur during assembly are similar within RNA viruses. The formation of virus particles ensures the efficient transmission of the RNA genome from one host cell to another within a single host or among different host organisms. The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules of linear, single-stranded RNAs of negative polarity, which encodes eleven (some influenza A strains ten) polypeptides, including: the RNA-dependent RNA polymerase proteins (PB2, PB1 and PA) and nucleoprotein (NP) which form the nucleocapsid; the matrix membrane proteins (M1, M2 or BM2); two surface glycoproteins which project from the lipid containing envelope: hemagglutinin (HA) and neuraminidase (NA); the nonstructural protein (NS1) and nuclear export protein (NEP). Most influenza A strains also encode an eleventh protein (PB1-F2) believed to have proapoptotic properties, whereas only influenza B viruses express the NB protein that might contribute to viral virulence (Hatta and Kawaoka, 2003, J. Virol., 77, 6050-6054). There are further minor differences between influenza A and B viruses in their expression strategies of gene products encoded by the viral NA and M gene segments (Lamb and Horvath, 1991, Trends Genet. 7:261-266). Significant biological and epidemiological differences are indicated by the almost exclusive confinement of influenza B viruses to humans, although there have already been studies isolating influenza B virus from seals indicating that there might also be a bigger reservoir of different organisms. Influenza A viruses have a very broad reservoir in many avian and mammalian species.

Transcription and replication of the genome takes place in the nucleus and assembly occurs via budding from the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced during influenza A replication, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for eleven proteins: nine structural and 2 non-structural (NS1 and the recently identified PB1-F2) proteins. Influenza B uses a different coding strategy for 2 proteins, namely NB and BM2. The former is translated from an overlapping reading frame of the NA gene and the latter is expressed via an overlapping stop-start codon from the M gene.

Vaccination is presently seen as the best way to protect humans against influenza. When healthy adults get immunized, currently available vaccines prevent clinical disease in 70-90% of cases. This level is reduced to 30-70% in those over the age of 65 and drops still further in those over 65 living in nursing homes (Strategic Perspective 2001: The Antiviral Market. Datamonitor. p. 59). The virus's frequent antigenic changes further contribute to a large death toll because not even annual vaccination can guarantee protection.

Vaccination is accomplished with commercially available, chemically inactivated (killed) or live attenuated influenza virus vaccines. Unfortunately, inactivated vaccines can hardly induce cross-protective immunity and therefore the vaccine strain must exactly fit to the antigenic properties of the future unknown pandemic strain.

Replication deficient influenza A viruses are supposed to overcome the safety issues in view of viral shedding. These can be influenza A mutants having deletions of the NS1 protein. The absence of the NS1 protein renders this virus replication-deficient in the respiratory tract of vaccinated mammalians. Upon intranasal administration, the vaccine virus is able to initiate abortive infection in mucosal tissues, without the effect of viral shedding. At the same time the virus stimulates local cytokine response and evokes a B- and T-cell mediated protective immune response.

Influenza B viruses mostly require laborious and time consuming adaptation to reach sufficient growth on Vero cells. Influenza B NS1 mutants which are able to replicate to high titres on Vero cells in addition to an interferon sensitive phenotype due to the abrogated function of NS1 are not described in the literature. Currently, the only published influenza B virus completely lacking the NS1 ORF does not replicate efficiently in Vero cells (titres of 1.7-2.5*$10^2$ FFU/ml using an moi of 0.1 and no detectable titres at moi of 0,001, respectively. Dauber et. al; Journal of Virology, February 2004, p. 1865-1872). An influenza B NS1 deletion mutant consisting of the amino-terminal 16 aa is also highly attenuated in replication with maximum titres of approx. $10^4$ FFU/ml. (Hai et. Al; Journal of Virology; November 2008, p. 10580-90

Reflecting the need to develop vaccine formulations of high safety containing influenza B antigenic compounds, there is a great demand in developing influenza B strains which are attenuated due to the abrogated function of NS1 but still show high growth properties in cell culture.

SHORT DESCRIPTION OF THE INVENTION

Clinical isolates of influenza B viruses normally require laborious and time consuming adaptation to reach high growth on Vero cells. For influenza A viruses not only wild type viruses but also mutants expressing a truncated NS1 protein of e.g. 38 amino acids or mutants completely lacking the NS1 ORF are able to replicate to high titres on interferon deficient Vero cells. This finding was used to produce a replication deficient attenuated influenza A live vaccine.

Up to now, this concept could not be applied for influenza B viruses due to the incompatibility of mutants with non functional NS1 protein to grow to high titres in tissue culture.

The inventors have now surprisingly shown that growth capabilities can be highly increased by modifying selected nucleotides proximal to the N-terminal region of the M gene of the influenza B virus genome. The M gene of influenza B viruses is of approx. 1.076 bp length, comprising the M1 and BM2 ORFs.

Further the invention also covers recombinant influenza B viruses comprising said modified M gene. Preferably the B viruses are replication deficient or at least attenuated, for example due to deletions within the NS1 protein.

Specifically a recombinant influenza B strain comprising a modification at any one of amino acid positions 82 to 90, preferably at any one of amino acid positions 85 to 87, preferably at amino acid position 86 in the M1 protein., a modified NS1 segment coding for a NS1 protein lacking a functional RNA binding domain and carboxy terminal domain and optionally a silent mutation at nucleotide position 950 of the M gene is covered by the present invention.

Further, vaccine formulations containing the inventive virus and methods for the prophylactic treatment of influenza as well as methods of making the inventive virus are covered.

The present invention also covers an isolated nucleic acid encoding the influenza virus M gene of the invention and its production.

FIGURES

FIG. 1: Schematic translation profile of influenza B NS genes of wild-type, NS14, NS38, NS57 and NS80 (a) and wild-type and ΔNS1 (b)

Figure 2:
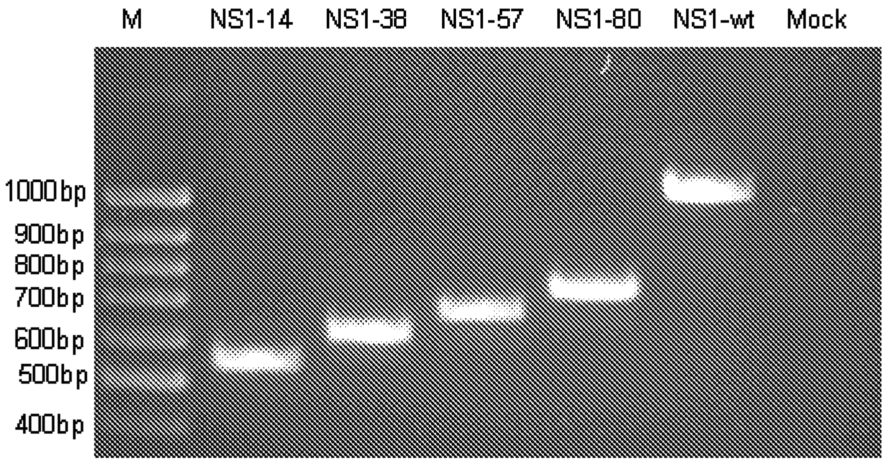

FIG. 2: RT-PCR products of the NS gene of indicated viruses expressing an NS1 protein of 14, 38, 57, 80 amino acids or wild-type NS1 respectively.

FIG. 3: Growth of influenza B/Malaysia viruses expressing an NS1 protein of 14, 38, 57 or 80 amino acids or wild-type NS1 respectively on Vero (a) and A549 cells (b)

FIG. 4: Viral titres of influenza B/Malaysia mutants with NS1 proteins of 38 or 80 amino acids or wt NS1 containing wt M gene or M1-M86V gene 6 days post transfection (a) and B/Florida mutants containing ΔNS1 gene or with NS1 proteins of 38 or 80 amino acids or wt NS1 containing wt M gene or M1-M86V gene 5 days post transfection (b).

FIG. 5: Amino acid comparison of the original B/Malaysia/2506/04-like swab M gene with the M1-M86V gene and other sequences published in the genebank.

Figure 6A:
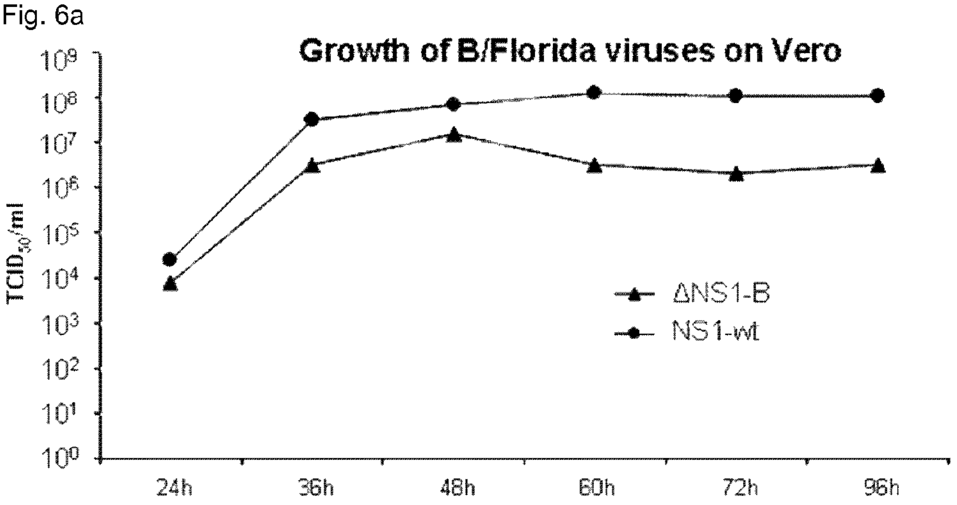
Figure 6B:
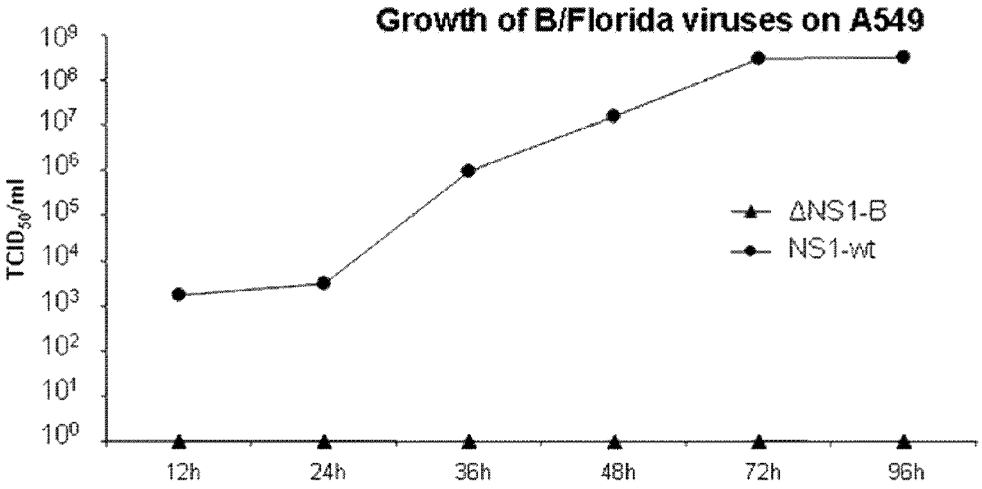

FIG. 6. Growth of influenza B/Florida viruses containing ΔNS1 gene or wild-type NS1 on Vero (a) and A549 cells (b).

FIG. 7: Amino acid sequence of the B/Vienna/33/06 M1 protein containing the M86V mutation (marked with bold letters, SEQ ID No. 1) (a) and B/Thüringen/02/06 M1 protein containing the M86V mutation (marked with bold letters, SEQ ID No. 2) (b).

Figure 10:
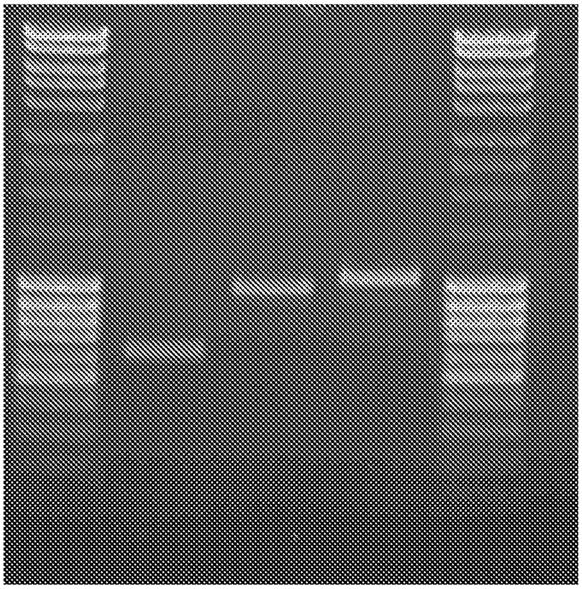

FIG. 8: Overview of constructed influenza B NS mutants. Genetic composition of all constructed influenza B Mutants (a); nucleotide sequence of B/Vienna/33/06 M gene M1-M86V, SEQ ID No. 3 (b); nucleotide sequence of B/Vienna/33/06 M gene M1-M86V and C950T, SEQ ID No. 4 (c); nucleotide sequence of B/Thüringen/02/06 M gene M1-wt, SEQ ID No. 5 (d); nucleotide sequence of B/Thüringen/02/06 M gene M1-M86V, SEQ ID No. 6 (e); nucleotide sequence of B/Vienna/33/06 M gene M1-C950T, SEQ ID No. 7 (f); nucleotide sequence of B/Vienna/33/06 NS gene of NS14, SEQ ID No. 8 (g); nucleotide sequence of B/Vienna/33/06 NS gene of NS38, SEQ ID No. 9 (h); nucleotide sequence of B/Vienna/33/06 NS gene of NS57, SEQ ID No. 10, (i); nucleotide sequence of B/Vienna/33/06 NS gene of NS64, SEQ ID No. 11 (j); nucleotide sequence of B/Vienna/33/06 NS gene of NS80, SEQ ID No. 12 (k); nucleotide sequence of B/Vienna/33/06 NS gene of ΔNS1-B, SEQ ID No. 13 (l); nucleotide sequence of B/Thüringen/02/06 NS gene of ΔNS1-B, SEQ ID No. 14 (m);

FIG. 9: Schematic translation profile of IL2 expressing influenza B Vectors with NS1 proteins of 38, 80, 104 and 145 aa length, respectively (a); genetic composition of all constructed IL2 expressing influenza B Vectors (b); nucleotide sequence of B/Vienna/33/06 NS gene of NS1-38IL2, SEQ ID No. 15 (c); nucleotide sequence of B/Vienna/33/06 NS gene of NS1-80IL2, SEQ ID No. 16 (d); nucleotide sequence of B/Vienna/33/06 NS gene of NS1-104IL2, SEQ ID No. 17 (e); nucleotide sequence of B/Vienna/33/06 NS gene of NS1-145IL2, SEQ ID No. 18 (f);

FIG. 10: RT-PCR products of influenza B/NS1-wt, B/NS1-38 and B/NS1-38IL2 viruses after 5 passages on Vero cells.

DETAILED DESCRIPTION OF THE INVENTION

The present invention provides a nucleotide sequence change of the M gene of influenza B virus which can increase the growth capabilities of the influenza B strain. Such changes can include deletions and substitutions. It has been successfully shown by the inventors that at least one a single amino acid change in the M1 protein of influenza B can lead to high growth properties in cell culture, especially in Vero cells. This specifically can enable the rescue of viruses expressing NS1 proteins of reduced length compared to wt NS1 proteins or mutants bearing a complete deletion in the NS1 ORF.

Specifically, influenza B virus M gene according to the present invention comprises a modification of at least one nucleotide of any one of nucleotide positions 265 to 294 of the M gene, preferably of at least one nucleotide at any one of nucleotide positions 277 to 285, more preferred of at least one nucleotide at any one of nucleotide positions 280 to 282.

Specifically, the modified M gene contains nucleotides GTG at positions 280 to 282 instead of ATG of the corresponding sequence of the isolated virus. Alternatively the modified M gene can also contain nucleotides GTA, GTC, GTT at positions 280 to 282. Of course, the embodiment also covers the respective RNA codons, GUG, GUA, GUC, GUU.

According to an alternative embodiment of the present invention the influenza B virus M gene comprises at least one nucleotide modification which results in at least one amino acid substitution at any one of amino acid positions 82 to 90, preferably at any one of amino acid positions 85 to 87, preferably at amino acid position 86 in the M1 protein. The substituted amino acid can be any amino acid; a non-polar, hydrophobic amino acid being preferred. Specifically, the amino acid change leads to the change of Methionine to Valine at amino acid position 86.

An M1 protein comprising at least one amino acid substitution at any one of amino acid positions 82 to 90, preferably at any one of amino acid positions 85 to 87, preferably at amino acid position 86 in the M1 protein is of course covered by the invention. The substituted amino acid can be any amino acid; a non-polar, hydrophobic amino acid being preferred. Specifically, the amino acid change leads to the change of Methionine to Valine at amino acid position 86. The M1 protein can be generated by any method as known in the art.

The term "amino acid substitution" refers to the presence of a modified or different amino acid at a particular location in the parenteral amino acid sequence of that molecule. The amino acid substitute occurs relative to any other amino acid that could have occupied that position. The polypeptide that results from the amino acid sequence change may include changes in post-translational modifications such as glycosylations, acetylations, phosphorylations or any other amino acid modification as well as the amino acid substitution.

A recombinant influenza B virus comprising the influenza virus M gene of the invention is also covered by the present invention.

Within other aspects a replication-deficient influenza viruses containing a modified M gene according to the invention can further contain a modification within the NS gene, specifically lack of part of or lack of the entire NS1 protein (ΔNS1). Due to the truncation or lack of expression of the NS1 protein, such viruses can replicate only in interferon-deficient cells but have lost their ability to grow in common hosts and organisms.

The NS1 protein of influenza A virus is a multifunctional protein that consists of approximately 230 amino acids and is early and abundantly synthesized in infection. It counters cellular antiviral activities and is a virulence factor. By the activity of its carboxy terminal region, the NS1 protein is able to inhibit the host mRNA's processing mechanisms. Second, it facilitates the preferential translation of viral mRNA by direct interaction with the cellular translation initiation factor. Third, by binding to dsRNA and interaction with putative cellular kinase(s), the NS1 protein is able to prevent the activation of interferon (IFN-) inducible dsRNA-activated kinase (PKR), 2'5' oligoadenylate synthetase system and cytokine transcription factors. Fourth, the N terminal part of NS1 binds to RIG-I and inhibits downstream activation of IRF-3, preventing the transcriptional induction of IFN-β. Therefore the NS1 protein inhibits the expression of INF-α or INF-β genes, delays the development of apoptosis in the infected cells, and prevents the formation of the antiviral state in neighbouring cells.

Influenza B viruses express from an unspliced transcript of the viral NS segment a 281-amino acid nonstructural protein termed NS1-B that shares with its NS1-A counterpart the ability to bind the same RNA targets and to inhibit PKR activation in vitro. In contrast to influenza A, influenza B NS1 does not inhibit pre-mRNA splicing but binds to the interferon-stimulated gene 15 (ISG15) product and inhibit its conjugation to cellular targets Influenza A viruses containing modifications within the NS1 protein are known in the art. For example, WO 99/64571 describes the complete knock out of the NS1 gene segment, WO 99/64068 discloses various NS1 gene segments that have been partially deleted. These publications are incorporated herein in full by reference. Only few influenza B viruses containing modifications in the NS1 protein are currently known and none of those viruses bearing an interferon sensitive phenotype due to the abrogated function in NS1 grows to high titres in Vero cells. Here, the construction of such viruses with modifications in the NS1 protein is described.

According to the present invention the modification within the NS1 protein can be a deletion, an insertion or substitution of at least one amino acid resulting in a replication deficient influenza virus.

Preferably the modified influenza B NS1 protein comprises a deletion of at least 50% of the NS1 amino acids, preferably of at least 70%, more preferably of at least 90%. Alternatively, the functionality of the NS1 protein can be completely diminished.

The NS1 protein of the influenza virus according to the invention can lack the functional RNA binding domain. The primary function of this domain located at the amino end of the NS1 protein (amino acids 1-93) is binding dsRNA and inhibiting the activation of PKR (Dauber et al, J. Virol. 2006 December; 80(23):11667-77).

According to the invention, the term functional carboxy terminal domain can comprise the region within the NS1 protein that enables the inhibition of the host mRNA's processing mechanisms, i.e. its activity suppresses the IFN response of the host cells.

Influenza B-NS1 seems to lack a carboxy terminal effector domain with similar function than influenza A-NS1. The C-terminal domain of the NS1 protein (amino acid positions 84 to 281) of influenza B virus is mainly responsible for inhibition of the IFN-α/β response (Dauber et al, J. Virol. 2006 December; 80(23):11667-77).

According to the invention, the carboxy terminal domain of the influenza B NS1 protein might be rendered non functional. This domain can be completely or partially deleted as well as amino acids can be substituted or inserted and the remaining domain can be tested for functionality as described in the art (Dauber et al, J. Virol. 2006 December; 80(23): 11667-77).

An inventive mutation of the M gene enables the generation of influenza B mutants which express a truncated NS1 protein (e.g. shorter than 80 amino acids) therefore bearing an interferon sensitive phenotype. Such mutants could be used especially as live attenuated vaccine strains of high safety and efficacy.

The inventive modification within the M gene can specifically increase the growth capabilities of said replication deficient influenza B. For example, an influenza B virus expressing a NS1 protein of 80 amino acids (NS1-80) containing the M1-M86V mutation achieved titres in a range of $5*10^5$ to $5*10^7$ $TCID_{50}$ whereas a similar virus with wt M1 protein grows to only $3*10^3$-$3*10^5$ $TCID_{50}$. Viruses containing a NS1 protein shorter than 80 amino acids i.e. 14, 38, 57 or 64 amino acids were only rescued using the inventive modification in the M gene and grew to titres ranging from $1*10^4$-$3*10^8$ $TCID^{50}$. The M1-M86V mutation can also be introduced into the backbone of another influenza B virus of different genetic subtype (for example Jiangsu/10/03-like) to prove, that the improved growth capacity especially of NS1 truncation mutants is rather universal than strain specific. In this backbone, the inventive M1-M86V mutation enabled the generation of a ΔNS1-B virus, in which the NS1 ORF is completely deleted, growing to high titres in the range of $10^7$ to $10^8$ $TCID_{50}$/ml in Vero cells.

According to a specific embodiment of the invention the recombinant influenza virus can comprise a) a modification at amino acid position 86 of the M1 protein
b) a modified NS1 segment coding for an NS1 protein lacking a functional RNA binding domain and functional carboxy terminal domain and
c) optionally a silent mutation at nucleotide position 950 of the M gene.

As an alternative embodiment of the invention, the recombinant replication deficient influenza B virus can also be used as a vehicle for expressing heterologous sequences, e.g. for the expression of chemokines or cytokines or fragments thereof.

More specifically it can be a recombinant influenza virus comprising a. a modification at amino acid position 86 of the M1 protein
b. a modified NS1 segment coding for a NS1 protein lacking a functional RNA binding domain and functional carboxy terminal domain and
c. a heterologous sequence inserted between the splice donor site and the splice acceptor site of the NS1 gene segment.

optionally a silent mutation at nucleotide position 950 of the M gene.

According to a preferred embodiment of the invention the heterologous sequence expresses cytokines or chemokines or fragments or derivatives thereof.

Cytokines are small secreted proteins which mediate and regulate immunity, inflammation and hematopoiesis. The largest group of cytokines are those which promote proliferation and differentiation of immune cells. Included within this group are interleukins, which are cytokines produced by leukocytes, and interferons, which may be produced by a variety of cell types.

Interferons (IFN) are a family of naturally occurring glycoproteins produced by cells of the immune system of vertebrates, including mammals, birds, reptiles and fish, in response to challenge by agents such as bacteria, viruses, parasites and tumour cells. In humans there are three major classes of interferons. The type I interferons include 14 IFN-alpha subtypes and single IFN-beta, omega, kappa and epsilon isoforms. Type II interferons consist of IFN-gamma and a recently discovered third class consists of IFN-lambda with three different isoforms.

Th1 cells secrete mainly IL-2, IFN-γ, and TNF-β, whereas Th2 cells which are relevant in humoral immune responses secrete cytokines such as IL-4, IL-5, and IL-10. Th2-type cytokines mediate delayed type hypersensitivity responses against intracellular pathogens and inhibit the Th1 responses.

Chemokines, originally derived from chemoattractant cytokines, actually comprise more than 50 members and represent a family of small, inducible, and secreted proteins of low molecular weight (6-12 kDa in their monomeric form) that play a decisive role during immunosurveillance and inflammatory processes. Depending on their function in immunity and inflammation, they can be distinguished into two classes. Inflammatory chemokines are produced by many different tissue cells as well as by immigrating leukocytes in response to bacterial toxins and inflammatory cytokines like IL-1, TNF and interferons. Their main function is to recruit leukocytes for host defence and in the process of inflammation. Homing chemokines, on the other hand, are expressed constitutively in defined areas of the lymphoid tissues. They direct the traffic and homing of lymphocytes and dendritic cells within the immune system. These chemokines, as illustrated by BCA-I, SDF-1 or SLC, control the relocation and recirculation of lymphocytes in the context of maturation, differentiation, activation and ensure their correct homing within secondary lymphoid organs.

According to the present invention it has been shown that biologically active cytokines or chemokines or derivatives or fragments thereof can be stably and efficiently expressed using an open reading frame different from the ORF expressing the NS1 protein. Alternatively additional leader sequences other than the natural signal peptides can be fused to the cytokines or chemokines which may further support efficient secretion of the protein and show a highly efficient induction of immune response in vivo.

Surprisingly, chemokines and cytokines can also be efficiently expressed when the amino acid sequence corresponding to the mature cytokine/chemokine is fused to a part of the NS1 protein via an amino acid sequence acting as a signal peptide, For example, this can be a part of the mouse IgKappa signal peptide.

According to the present invention the heterologous sequence preferably codes for interleukin 2 (IL-2) or a fragment or derivative thereof. IL-2 comprises secretory signal sequences and is an immunomodulatory, T-cell derived molecule required for the clonal expansion of antigen-activated T-cells. The secretion of IL-2 by CD4+T lymphocytes has multiple biological effects, such as the induction of proliferation of T-helper and T-killer cells and the stimulation of T-cells to produce other cytokines. Furthermore, IL-2 can also activate B-cells, NK cells and macrophages. When IL-2 is expressed from recombinant viruses infecting non-lymphoid cells, its secretion could significantly decrease the pathogenesis of viral infection and modify the immune response. It is also known that IL-2 acts as immune adjuvant.

According to the present invention any fragment or derivative of the cytokines and chemokines is included that is still biologically active, i.e. shows immunomodulatory activities.

Alternatively, the cytokines/chemokines can also be selected from the group consisting of IL-15, GM-CSF, CCL3 or CCL20 or derivatives or fragments thereof.

Alternatively, it can be also any epitope or immunomodulatory region derived from Mycobacterium tuberculosis, for example ESAT-6.

Alternatively the heterologous sequences can also comprise chimeric proteins being cytokines or chemokines or fragments or derivatives thereof fused to antigenic proteins or antigenic peptides. Fusion can be either directly or via peptide linker sequences having a length of at least 4 amino acids, preferably at least 5 amino acids. For example, the linker sequences according to the invention are GGGS or GGGGS.

Examples for IL-2 chimeric proteins are known in the art. Exemplarily, this could be IL-2-PE40 (wherein PE is Pseudomonas exotoxin A), DAB389-IL-2 (where DAB is diphtheria toxin) or IL-2 Bax (wherein Bax is a proapoptotic protein of human origin) (Aqeilan R. et al., Biochem. J., 2003, 129-140).

According to the present invention the nucleotide sequences of the heterologous sequences which are introduced into the replication deficient influenza vector show at least 80% identity with their native sequences, preferably at least 85% identity, more preferred at least 90% identity. Any optimization of the nucleotide sequence in view of codon usage is included thereby.

Alternatively, the heterologous sequence can comprise B-cell or T-cell-epitopes, for example a B cell epitope from influenza hemagglutinin (HATB), for example the A loop epitope from the influenza virus hemagglutinin (HA) or parts thereof, or peptides representing one of the immunodominant epitopes of HA corresponding to amino acid sequence 150 to 159 (Caton et al., 1982, Cell, 417-427).

The epitope can also be derived from melanoma-associated endogenous retrovirus (MERV) as described in WO06/119527.

According to a specific embodiment, the NS1 gene segment can contain a functional natural splice donor and acceptor splice site, i.e. the splice donor and acceptor sites are kept as natural sites, i.e. the nucleotides are not modified by artificial techniques.

Any nucleotide modifications at the splice sites occurring naturally due to modifications of influenza viruses based on environmental adaptations or natural strain developments are natural modifications and do not fall under the term synthetic or artificial modifications.

Alternatively, the sequences surrounding the splice donor and/or upstream of the acceptor site can be altered, Preferably, alteration or modification can be performed within 3 nucleotides 5' to the and/or 8 nucleotides 3' to the 5' border of the NS intron, as well as 100 nucleotides 5' to the and/or 2 nucleotides 3' to the 3' border of the NS intron. This is preferably by introducing synthetic sequences in order to modify splicing activity.

If e.g. insertion of a heterologous sequence increases NS intron size it may be preferable to modify the sequences surrounding the splice donor and/or acceptor site in order to increase splicing efficacy and thus genetic stability of the recombinant NS segment.

For example, it can be modified in that either the sequence surrounding the splice donor site is altered to increase the homology to the 5'end of the human U1 snRNA and/or the sequence upstream of the splice acceptor site containing the branch point (Plotch et al. 1986, Proc Natl Acad Sci USA. 83:5444-8; Nemeroff et al. 1992, Mol Cell Biol. 12:962-70) and the pyrimidine stretch is replaced by a sequence that enhances splicing of the NS segment.

In order to optimize splicing, the a preferred sequence introduced 5' of the splice acceptor site comprises a lariat consensus sequence and a pyrimidine stretch.

In view of stability of the virus vector and the expression rate of the heterologous sequence it can be important to introduce the synthetic/modified sequence containing a lariat consensus sequence and a pyrimidine stretch at a specific position within the NS gene, e.g. directly upstream of the slice acceptor site.

Furthermore, it may be necessary to vary the distance between the lariat consensus sequence and the pyrimidine stretch to modify the splicing rate of the NS segment (Plotch S. and Krug R., 1986, Proc. Natl. Acad. Sci., 83, 5444-5448; Nemeroff M. et al., 1992, Mol. Cell. Biol., 962-970).

For example, the recombinant influenza B strain can comprise an amino acid sequence as shown in SEQ ID. No. 1 or 2 or a nucleotide sequence as shown in any one of SEQ ID Nos. 3 to 18 or a derivative thereof having at least 98% sequence identity, preferably at least 99% sequence identity, preferably at least 99.5%.

According to the invention, the term "recombinant" does cover all influenza strains that have been produced using recombinant techniques like, for example, reverse genetics technology. Therefore the influenza strains according to the invention contain a modification within the M gene but need not contain any further modifications within the nucleotide or amino acid sequence compared to the parental strain.

Also a vaccine composition comprising an immunogenically-inducing effective amount of virus in admixture with a pharmaceutically acceptable carrier is covered. Adjuvants can also be contained in the composition.

According to the invention the term "immunogenic" means that the virus is capable of eliciting humoral or cellular immune response, and preferably both. An immunogenic entity is antigenic, too. An immunogenically inducing effective amount of virus elicits humoral or cellular immune response, or both, when administered to an animal, preferably to a human.

The vaccine composition may be used for prophylactic treatment of influenza disease comprising administering to a human patient in need of treatment an immunologically inducing effective amount of the composition.

Vaccine compositions can contain complete influenza B virus according to the invention but also reassortant strains wherein part of the viral segments are derived from different influenza B strains and segments, especially M1 protein is derived from the recombinant influenza B virus according to the invention. The inventive M1-M86V mutation could be further introduced into any other influenza B strain.

The compositions may be used in methods or as medicaments in preventing, managing, neutralizing, treating and/or ameliorating influenza virus infection. The use of an influenza virus M molecule according to the invention in the manufacture of a medicament for treatment of an influenza virus infection is of course included.

The immunogenic compositions may comprise either a live or inactivated influenza B virus of the invention. The virus can be inactivated by methods well known to those of skill in the art. Common methods use formalin and heat for inactivation.

A live immunogenic formulation may be preferred due to increased immunogenicity. Production of such live recombinant immunogenic formulations may be accomplished using conventional methods involving propagation of the virus in cell culture or in embryonated eggs (e.g., embryonated chicken eggs) followed by purification.

The term "pharmaceutically acceptable" means approved by a regulatory agency of the Federal or a state government or listed in the U.S.

The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The particular formulation may also depend on whether the virus is live or inactivated.

The term adjuvant refers to a compound or mixture that enhances the immune response to an antigen.

The prophylactic and/or therapeutic effect of the immunogenic formulations of the invention is based, in part, upon achieving or inducing an immune response (e.g., a humoral immune response). In one aspect, the immunogenic formulations induce a detectable serum titer of an antibody against antigens of the influenza B virus in either the subject or an animal model thereof (e.g. mouse, ferret, rat or canine model). The serum titer of an antibody can be determined using techniques known to one of skill in the art, e.g., immunoassays such as ELISAs or hemagglutinin inhibition tests.

According to the invention also a method of generating a virus is also covered wherein the method comprises using a recombinant expression system that expresses the inventive influenza virus M molecule. According to the present invention the expression system can be any plasmid useful, e.g. as described by Hoffmann et al. ((Hoffmann et al. 2000, Proc Natl Acad Sci USA. 97:6108-13) or a linear expression construct according to EP07450177.

For developing reassortants and/or expression of modified influenza virus strains a reverse genetics system on Vero cells can be used. The technology is already well known in the art (Pleschka S. et al., 1996, J. Virol., 70(6), 4188-4192, Neumann and Kawaoka, 1999, Adv. Virus Res., 53, 265-300, Hoffmann et al. 2000, Proc Natl Acad Sci USA. 97:6108-13)

The cells used for the cultivation of viruses using a cultivation medium can be any cells that can grow in vitro in synthetic media and can be used for the propagation of viruses. Within the scope of the invention, the term “cells” means the cultivation of individual cells, tissues, organs, insect cells, avian cells, mammalian cells, hybridoma cells, primary cells, continuous cell lines, and/or genetically engineered cells, such as recombinant cells expressing a virus. These can be for example BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells), chicken embryo cells or derivatives, embryonated egg cells, embryonated chicken eggs or derivatives thereof. Preferably the cell line is a VERO cell line.

The cultivation medium used for the production of viruses can be any medium known from prior art that is applicable for virus cultivation. Preferably the medium is a synthetic medium. This can be for example basal media as Modified Eagle’s media MEM, minimum essential media MEM, Dulbecco’s modified Eagle’s media D-MEM, D-MEM-F12 media, William’s E media, RPMI media and analogues and derivative thereof. These can also be specialty cell cultivation and virus growth media as VP-SFM, OptiPro™ SFM, AIM V® media, HyQ SFM4 MegaVir™, EX-CELL™ Vero SFM, EPISERF, ProVero, any 293 or CHO media and analogues and derivatives thereof. These media can be supplemented by any additive known from prior art that is applicable for cell and virus cultivation as for example animal sera and fractions or analogues thereof, amino acids, growth factors, hormones, buffers, trace elements, trypsin, sodium pyruvate, vitamins, L-glutamine and biological buffers. Preferable medium is OptiPRO™ SFM supplemented with L-glutamine and trypsin.

Using the inventive modification of the M gene the growth rate of influenza B NS1 truncation mutants can be increased at least by a factor of approx 100-1000 as demonstrated for the NS1-38 virus, when the viral titers ($TCID_{50}$) between the unmodified and improved M genes were compared. For influenza B viruses expressing a NS1 protein of 14, 57 or 80 amino acids, respectively, the mutation is in the M gene is absolutely required to generate such viruses. These viruses can grow up to a titre of approx $10^6$-$10^8$ $TCID_{50}$ A further embodiment of the invention is an isolated nucleic acid encoding the inventive influenza virus M gene and/or a recombinant influenza virus B containing the modified M gene.

Further a method for preparing said nucleic acid according which method comprises introducing a nucleotide sequence into a vector encoding the inventive M molecule. If a DNA vector is used, said vector is a transcription system for minus sense influenza RNA. For example it can be a vector as used by Hoffmann et al., 2000, Proc Natl Acad Sci USA. 97:6108-13.

The foregoing description will be more fully understood with reference to the following examples. Such examples are, however, merely representative of methods of practicing one or more embodiments of the present invention and should not be read as limiting the scope of invention.

EXAMPLES

Example 1

Influenza B Viruses Expressing Truncated NS1 Proteins for Usage as a Replication Deficient Live Attenuated Influenza Vaccine.

Figure 1B:
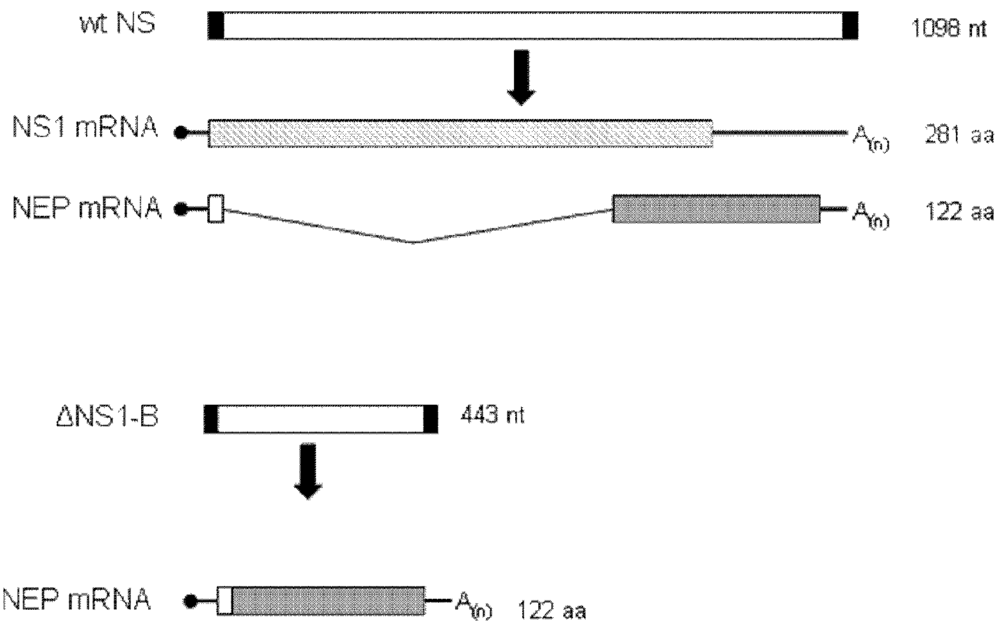

A reverse genetic system for the construction of a Vero adapted influenza B strain (B/Vienna/33/06 subtyped as B/Malaysia/2506/04) as a representative of the B/Victoria/2/87 linage was generated (Hoffmann et. al 2000, PNAS 97(11):6108-13.). HA and NA were cloned from influenza B/Thüringen/02/06 (B/Jiangsu/10/03-like). By introducing a coding mutation in the M1 protein (change from methionine to valine at amino acid position 86), influenza mutants expressing a truncated version of the NS1 protein of 14, 38, 57 and 80 amino acids could be obtained and named B/Malaysia NS1-14, NS1-38, NS1-57 or NS1-80 respectively. The translation of NS1 was terminated by two consecutive, in frame stop codons and the non translated part downstream of the stop codons up to the splicing signal of NEP was deleted (FIG. 1*a*). Due to the different lengths of the NS gene, the viruses containing NS1 proteins of different lengths could be distinguished according to their size by RT-PCR (FIG. 2). All generated mutants were replicating to high titres on Interferon deficient Vero cells (FIG. 3*a*) but were attenuated on interferon competent A549 cells (FIG. 3*b*

Figure 3A:
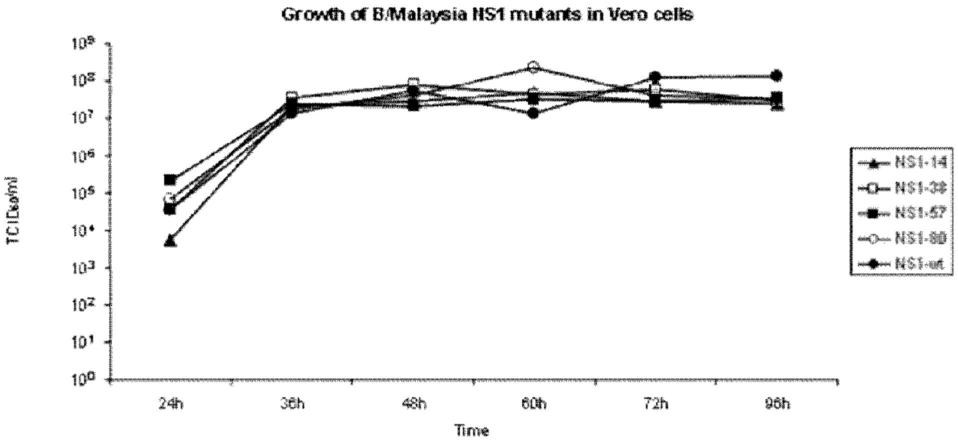
Figure 3B:
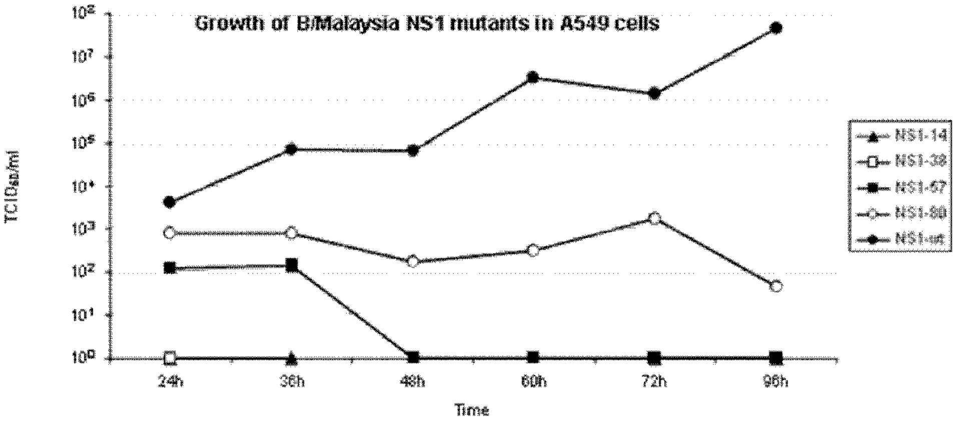
Figure 4A:
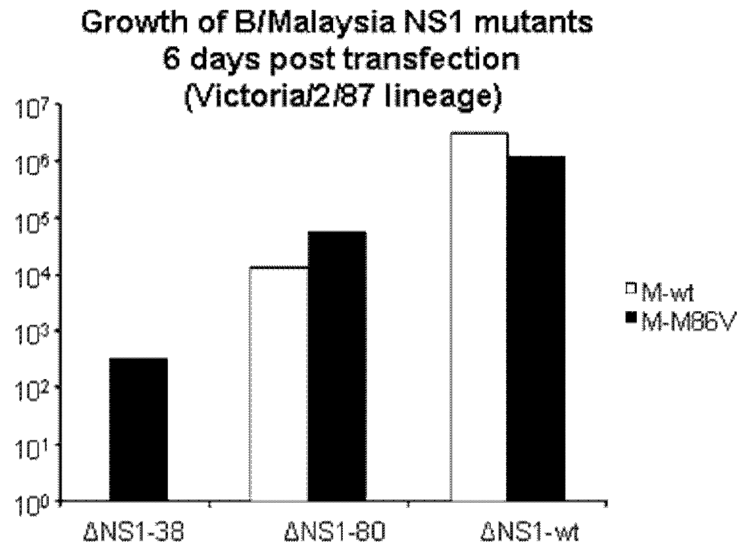

The inventive modification within the M gene can specifically increase the growth capabilities of said replication deficient influenza B viruses. For example, an influenza B virus expressing a NS1 protein of 80 amino acids (NS1-80) containing the M1-M86V mutation grows to titres of approx. $5,62*10^4$ $TCID_{50}$ in contrast to titres of approx. $1,33*10^4$ $TCID_{50}$ of a similar virus which does not contain any modification in M1 when analyzed 6 days post transfection (FIG. 4*a*). An influenza B virus expressing a NS1 protein of 38 amino acids (NS1-38) could not be rescued at all without the adapting M1 mutation but grows to average titres of approx. $3,16*10^2$ $TCID_{50}$ when the M1-M86V mutation was introduced (FIG. 4*a*). This effect was even more pronounced in the $2^{nd}$ passage post transfection, reflected by titres (Table 1). The same rescue efficiency was observed with influenza B viruses expressing an NS1 protein of 14, or 57 amino acids, respectively, which were only rescued in the presence of the M1-M86V mutation (data not shown). Further adaptive passages on Vero cells resulted in high titres ranging from 6.5-8.5 logs $TCID_{50}$ which are required for efficient vaccine production, of all NS1 mutants (FIG. 3*a*). The inventive mutation might have no or only minor effect on the growth of wt NS1 viruses. The wt NS1 influenza B virus containing the non-modified M gene even grew to slightly higher titres than the analogous virus containing the M1-M86V mutation 6 days post transfection (FIG. 4*a*) and in the $2^{nd}$ passage after transfection (Table 1). This can be interpreted by the variation of growth between the different passages as demonstrated by the growth of the $1^{st}$ Passage after transfection ($1,78*10^7$ $TCID_{50}$ with wt M gene in comparison to $2,82*10^7$ $TCID_{50}$ with M1-M86V, both containing wt NS gene)

TABLE 1

| | $TCID_{50}$ $2^{nd}$ Passge after Transfection | |
|---|---|---|
| | wt M1 | M1-M86V |
| wt NS | 1.00E+07 | 1.00E+06 |
| NS1-80 | 3.16E+05 | 1.78E+07 |
| NS1-38 | 0.00E+00 | 2.31E+04 |

Viral titres (TCID50) of influenza B viruses with wt, NS80 or NS38 NS1 protein in combination with either wt or M1-M86V M gene 4 days post infection analyzed in the $2^{nd}$ passage after transfection.

Therefore, only this novel mutation enables the generation of influenza B mutants which express a short NS1 protein (i.e. comprising less than the first N-terminal 80 amino acids) with non-functional NS1, therefore bearing an interferon sensitive phenotype. Such mutants could be consequently used as vaccine strains. This mutation was never described before nor was it found it the NIBSC sequencing database. FIG. 5 shows a sequence comparison of the M gene original B/Malaysia/2506/04-like swab with the M1-M86V gene and other sequences published in the genebank.

Example 2

The Inventive Mutation in the M1 Protein (M86V) Enables the Generation of Influenza B Viruses with Truncated NS1 Proteins on Vero Cells in Different Influenza B Lineages.

Figure 4B:
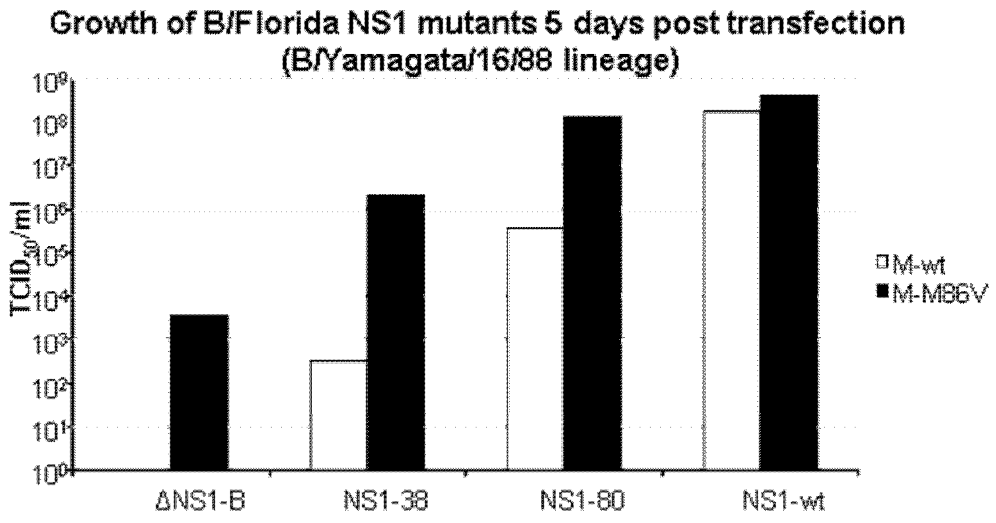

To test the influence of the M1-M86V mutation in other influenza B strains, a reverse genetic system for the generation of influenza B/Thüringen/02/06 (B/Jiangsu/10/03-like) as a representative of the B/Yamagata/16/88 linage was generated and the described mutation in the M1 protein (M86V) was introduced. To follow the WHO recommendation for the influenza vaccine strains for the season 2008/2009 in the northern hemisphere, HA and NA of a B/Florida/04/06-like virus were used. Influenza B mutants expressing a truncated version of the NS1 protein of 38 and 80 amino acids or a mutant with a complete deletion in the NS1 ORF (ΔNS1-B) (FIG. 1*b*), in which NS2/NEP is expressed as a monicistronic RNA were obtained and named B/Florida NS1-38, NS1-80 or ΔNS1-B, respectively. As was the case with the mutants of B/Malaysia, a representative of the B/Victoria/2/87 lineage, the M1-M86V mutation had only a small impact on the rescue efficacy of NS1-80 and NS1-wt viruses of the B/Florida, a representative of the Yamagata lineage (FIG. 4*b*). This was demonstrated by slightly increased titers 5 days post transfection as compared to mutants containing the wt M gene (FIG. 4*b*). Viral titers for the NS1-38 mutant containing the M1-M86V mutation were approximately 4 logs higher than wt M1 analogs. Due to the M1-M86V mutation, we were able to rescue a ΔNS1-B virus reaching titers of almost 4 logs 5 days post transfection (FIG. 4*b*). In order to demonstrate the replication-deficient phenotype of ΔNS1-B virus, we examined its ability to grow on IFN-deficient Vero (FIG. 6*a*) and IFN-competent A549 (FIG. 6*b*) cells in comparison to the corresponding wt virus. Both viruses showed comparable growth kinetics on Vero cells, reaching titers in the range of $10^7$ to $10^8$ $TCID_{50}$/ml. Replication of ΔNS1-B virus was completely restricted in IFN-competent A549 cells, which displayed no growth above the detection limit of $2\times10^2$ $TCID_{50}$/ml, while NS1-wt virus replicated to high titers of $3{,}15\times10^8$ $TCID_{50}$/ml. Mutant viruses NS1-80 and NS1-38 showed intermediate replication capacity (data not shown).

These data show that the adaptive M1 mutation does not only have a growth-optimizing effect in one viral strain but also seems to be effective in other influenza B lineages. Moreover, the data demonstrate that this mutation is essential for rescuing a ΔNS1-B virus, in which the NS1 ORF is completely deleted, growing to high titers in Vero cells. Therefore, this is a universal concept for the generation of replication deficient influenza B viruses in which the attenuation mechanism is based on the removal of NS1, the major interferon antagonist.

Example 3

An Influenza B Virus Vector Expressing Human Interleukin 2 from the NS Gene Using a Bicistronic Expression Strategy as Potential Live Attenuated Influenza Vaccine with Improved Immunogenicity Especially in Elderly.

Figures 9A, 9B:
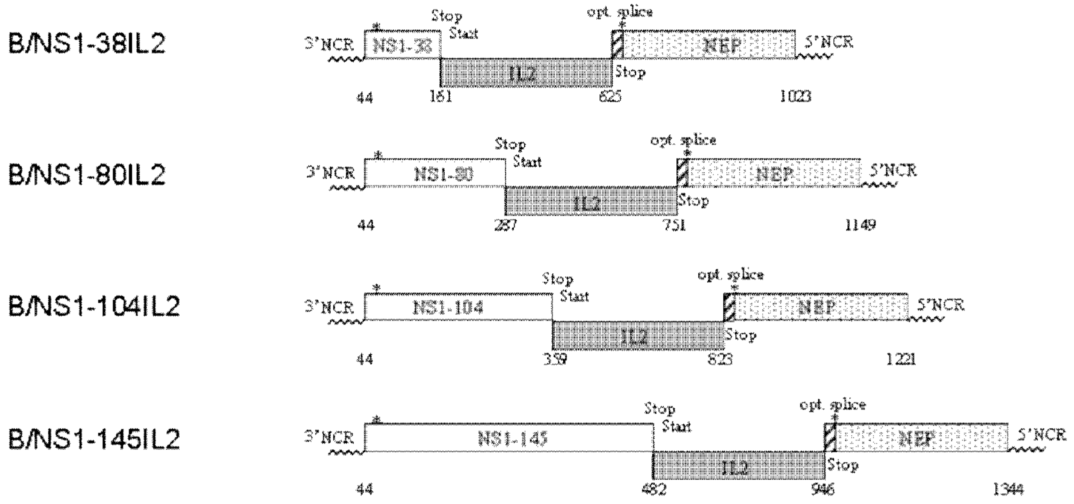

An overlapping Stop-Start codon cassette (TAATG) followed by the coding sequence of human IL2 was inserted after amino acid position 38, 80, 104 or 145 of the NS1 protein of an influenza B virus, respectively. In addition, a synthetic sequence of 29 nucleotides comprising a lariat consensus sequence followed by an optimized splice site, a 20-base pyrimidine stretch segment (opt. splice) replaces the part between the stop codon of IL2 and the splice acceptor site of NS2 (EP7450176.8). (FIG. 9*a*).

By introducing the inventive mutation in the M1 protein (M86V), we succeeded in rescuing an influenza B virus B/NS1-38IL2 in the backbone of influenza B/Thüringen/02/06 (B/Jiangsu/10/03-like). Without the inventive modification in the M1 protein, this virus was not rescued. Although growth of B/NS1-38IL2 was slightly lower compared to the "empty vector" B/NS1-38, a titer of more than 6 log 10 TCID50/ml was achieved (Table 2). This stock was further passaged five times on Vero cells to check genetic stability. No appearance of deletion mutants were found as demonstrated by the presence of RT-PCR bands of the expected size of the NS gene without appearance of smaller PCR bands potentially reflecting deletion mutants (FIG. 10).

Vero cells infected with B/NS1-38IL2 secreted high levels of more than 2.5 μg/ml IL2 in contrast to non detectable IL2 levels in non infected cells (mock), cells infected with B/NS1-38 or B/NS1-wt (Table 2). Such vectors could be used as live influenza vaccines with an increased immunogenicity especially in elderly as already demonstrated for influenza A (Ferko, Kittel et al 2006)

TABLE 2

| Replication in Vero cells and expression levels of human IL2 of indicated viruses | | |
|---|---|---|
| Virus | Titer [TCID50/ml] | Human IL2 ELISA [pg/ml] |
| B/NS1-wt | 2.88E+07 | <19 |
| B/NS1-38 | 1.78E+08 | <19 |
| B/NS1-38IL2 | 2.31E+06 | 2687 |
| Mock | — | <19 |

We investigated the immunogenicity of the generated viruses of all 3 examples. From these data we conclude, that the inventive M1-M86V mutation does not negatively influence the immunogenicity of the constructed viruses as demonstrated by comparable immunogenicity data of respective influenza A viruses.

The invention claimed is:

1. An influenza B virus M gene comprising SEQ ID NO:3, SEQ ID NO:4, or SEQ ID NO:6, or a nucleotide sequence which has at least 98% identity to the sequence of SEQ ID NO:3, SEQ ID NO:4, or SEQ ID NO:6 and encodes for a valine at position 86 of the M1 protein.

2. A recombinant influenza B virus comprising an influenza virus M gene of claim 1.

3. The recombinant virus of claim 2, wherein said virus is a reassortant virus.

4. The recombinant influenza B virus of claim 2, further comprising a modification within a NS gene, wherein the modification within said NS gene encodes for a modified NS1 protein lacking a functional RNA binding domain and a functional carboxy terminal domain.

5. The recombinant influenza B virus of claim 4, wherein the virus is attenuated or replication deficient.

6. The recombinant influenza B virus of claim 2, further comprising a silent mutation at nucleotide position 950 of the M gene of SEQ ID NO: 3, SEQ ID NO: 4, or SEQ ID NO: 6.

7. The recombinant influenza B virus of claim 2, further comprising a heterologous sequence inserted between a splice donor site and a splice acceptor site of a NS1 gene segment.

8. A vaccine composition comprising an immunogenically effective amount of the virus of claim 4 in admixture with a pharmaceutically acceptable carrier.

9. A method of treating or inhibiting an influenza B virus infection comprising administering to a subject the vaccine composition of claim 8.

10. The method of claim 9, wherein the recombinant influenza B virus of the vaccine composition further comprises a silent mutation at nucleotide position 950 of the M gene of SEQ ID NO: 3, SEQ ID NO:4, or SEQ ID NO: 6.

11. An isolated influenza B virus M1 protein comprising SEQ ID NO: 1 or SEQ ID NO: 2; or an amino acid sequence being at least 98% identical to the sequence of SEQ ID NO: 1 or SEQ ID NO: 2 and having a valine at position 86.

12. A recombinant influenza B virus comprising an influenza B virus M1 protein, wherein the protein comprises SEQ ID NO: 1 or SEQ ID NO: 2; or an amino acid sequence being at least 98% identical to the sequence of SEQ ID NO: 1 or SEQ ID NO: 2 and having a valine at position 86.

13. The recombinant influenza B virus of claim 12, wherein said virus is a reassortant virus.

14. The recombinant influenza B virus of claim 12, further comprising a modification within a NS gene, wherein the modification within said NS gene encodes for a modified NS1 protein lacking a functional RNA binding domain and a functional carboxy terminal domain.

15. The recombinant influenza B virus of claim 14, wherein the virus is attenuated or replication deficient.

16. The recombinant influenza B virus of claim 12, further comprising a silent mutation at nucleotide position 950 of the M gene that encodes SEQ ID NO: 1 or SEQ ID NO: 2.

17. The recombinant influenza B virus of claim 12, further comprising a heterologous sequence inserted between a splice donor site and a splice acceptor site of a NS1 gene segment.

18. A vaccine composition comprising an immunogenically effective amount of the virus of claim 14, in an admixture with a pharmaceutically acceptable carrier.

19. A method of treating or inhibiting an influenza B virus infection comprising administering to a subject the vaccine composition of claim 18.

20. The method of claim 19, wherein the recombinant influenza B virus of the vaccine composition further comprises a silent mutation at nucleotide position 950 of the M gene that encodes SEQ ID NO: 1 or SEQ ID NO: 2.

* * * * *

UNITED STATES PATENT AND TRADEMARK OFFICE

CERTIFICATE OF CORRECTION

PATENT NO. : 8,592,196 B2
APPLICATION NO. : 12/809814
DATED : November 26, 2013
INVENTOR(S) : Kittell It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 510 days.

Signed and Sealed this
Fourteenth Day of April, 2015

Michelle K. Lee
*Director of the United States Patent and Trademark Office*

SEQUENCE LISTING

<160> NUMBER OF SEQ ID NOS: 20

<210> SEQ ID NO 1
<211> LENGTH: 248
<212> TYPE: PRT
<213> ORGANISM: Influenza B virus

<400> SEQUENCE: 1

Met Ser Leu Phe Gly Asp Thr Ile Ala Tyr Leu Leu Ser Leu Thr Glu
1 5 10 15

Asp Gly Glu Gly Lys Ala Glu Leu Ala Glu Lys Leu His Cys Trp Phe
20 25 30

Gly Gly Lys Glu Phe Asp Leu Asp Ser Ala Leu Glu Trp Ile Lys Asn
35 40 45

Lys Arg Cys Leu Thr Asp Ile Gln Lys Ala Leu Ile Gly Ala Ser Ile
50 55 60

Cys Phe Leu Lys Pro Lys Asp Gln Glu Arg Lys Arg Arg Phe Ile Thr
65 70 75 80

Glu Pro Leu Ser Gly Val Gly Thr Thr Ala Thr Lys Lys Lys Gly Leu
85 90 95

Ile Leu Ala Glu Arg Lys Met Arg Arg Cys Val Ser Phe His Glu Ala
100 105 110

Phe Glu Ile Ala Glu Gly His Glu Ser Ser Ala Leu Leu Tyr Cys Leu
115 120 125

Met Val Met Tyr Leu Asn Pro Gly Asn Tyr Ser Met Gln Val Lys Leu
130 135 140

Gly Thr Leu Cys Ala Leu Cys Glu Lys Gln Ala Ser His Ser His Arg
145 150 155 160

Ala His Ser Arg Ala Ala Arg Ser Ser Val Pro Gly Val Arg Arg Glu
165 170 175

Met Gln Met Val Ser Ala Met Asn Thr Ala Lys Thr Met Asn Gly Met
180 185 190

Gly Lys Gly Glu Asp Val Gln Lys Leu Ala Glu Glu Leu Gln Ser Asn
195 200 205

Ile Gly Val Leu Arg Ser Leu Gly Ala Ser Gln Lys Asn Gly Glu Gly
210 215 220

Ile Ala Lys Asp Val Met Glu Val Leu Lys Gln Ser Ser Met Gly Asn
225 230 235 240

Ser Ala Leu Val Lys Lys Tyr Leu
245

<210> SEQ ID NO 2
<211> LENGTH: 248
<212> TYPE: PRT
<213> ORGANISM: Influenza B virus

<400> SEQUENCE: 2

Met Ser Leu Phe Gly Asp Thr Ile Ala Tyr Leu Leu Ser Leu Thr Glu
1 5 10 15

Asp Gly Glu Gly Lys Ala Glu Leu Ala Glu Lys Leu His Cys Trp Phe
20 25 30

Gly Gly Lys Glu Phe Asp Leu Asp Ser Ala Leu Glu Trp Ile Lys Asn
35 40 45

Lys Arg Cys Leu Thr Asp Ile Gln Lys Ala Leu Ile Gly Ala Ser Ile
50 55 60

-continued

```
Cys Phe Leu Lys Pro Lys Asp Gln Glu Arg Lys Arg Arg Phe Ile Thr
65                  70                  75                  80

Glu Pro Leu Ser Gly Val Gly Thr Thr Ala Thr Lys Lys Lys Gly Leu
                85                  90                  95

Ile Leu Ala Glu Arg Lys Met Arg Lys Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 3
<211> LENGTH: 1189
<212> TYPE: DNA
<213> ORGANISM: Influenza B virus

<400> SEQUENCE: 3

agcagaagca cgcactttct taaaatgtcg ctgtttggag acacaattgc ctacctgctt      60

tcattgacag aagatggaga aggcaaagca gaactagcag aaaaattaca ctgttggttt     120

ggtgggaaag aatttgacct agactctgcc ttggaatgga taaaaaacaa aagatgctta     180

actgatatac aaaaagcact aattggtgcc tctatatgct tttaaaacc caaagaccag      240

gaaagaaaaa gaagattcat cacagagccc ttatcaggag tgggaacaac agcaacaaaa     300

aagaaaggcc tgattctggc tgagagaaaa atgagaagat gtgtgagctt tcatgaagca     360

tttgaaatag cagaaggcca tgaaagctca gcgctactat actgtctcat ggtcatgtac     420

ctgaatcctg gaaattattc aatgcaagta aaactaggaa cgctctgtgc tttatgcgag     480

aaacaagcat cacattcaca cagggctcat agcagagcag cgagatcttc agtgcctgga     540

gtgagacgag aaatgcagat ggtctcagct atgaacacag caaaaacaat gaatggaatg     600

ggaaaaggag aagacgtcca aaagttggca gaagagctgc aaagcaacat tggagtgctg     660

agatctcttg ggcaagtcca aaagaatggg gaagggattg caaaggatgt aatggaagtg     720

ctaaagcaga gctccatggg aaattcagct cttgtgaaga aatatctata atgctcgaac     780

catttcagat tctttcaatt tgttctttta tcttatcagc tctccatttc atggcttgga     840

caatagggca tttgaatcaa ataaaaagag gaataaacat gaaaatacga ataaaaggtc     900

caaacaaaga gacaataaac agagaggtat caattttgag acacagttac caaaaagaaa     960

tccaggccaa agaaacaatg aaggaagtac tctctgacaa catggaggta ttgagtgacc    1020

acataataat tgaggggctt tctgccgaag agataataaa aatgggtgaa acagttttgg    1080
```

-continued agatagaaga attgcattaa attcaatttt actgtatttc ttactatgca tttaagcaaa 1140
ttgtaatcaa tgtcagcaaa taaactggaa aaagtgcgtt gtttctact 1189

<210> SEQ ID NO 4
<211> LENGTH: 1189
<212> TYPE: DNA
<213> ORGANISM: Influenza B virus

<400> SEQUENCE: 4
agcagaagca cgcactttct taaaatgtcg ctgtttggag acacaattgc ctacctgctt 60
tcattgacag aagatggaga aggcaaagca gaactagcag aaaaattaca ctgttggttt 120
ggtgggaaag aatttgacct agactctgcc ttggaatgga taaaaaacaa aagatgctta 180
actgatatac aaaaagcact aattggtgcc tctatatgct ttttaaaacc caaagaccag 240
gaaagaaaaa gaagattcat cacagagccc ttatcaggag tgggaacaac agcaacaaaa 300
aagaaaggcc tgattctggc tgagagaaaa atgagaagat gtgtgagctt tcatgaagca 360
tttgaaatag cagaaggcca tgaaagctca gcgctactat actgtctcat ggtcatgtac 420
ctgaatcctg gaaattattc aatgcaagta aaactaggaa cgctctgtgc tttatgcgag 480
aaacaagcat cacattcaca cagggctcat agcagagcag cgagatcttc agtgcctgga 540
gtgagacgag aaatgcagat ggtctcagct atgaacacag caaaaacaat gaatggaatg 600
ggaaaaggag aagacgtcca aaagttggca gaagagctgc aaagcaacat tggagtgctg 660
agatctcttg ggcaagtcaa aaagaatggg gaagggattg caaaggatgt aatggaagtg 720
ctaaagcaga gctccatggg aaattcagct cttgtgaaga aatatctata atgctcgaac 780
catttcagat tctttcaatt tgttctttta tcttatcagc tctccatttc atggcttgga 840
caatagggca tttgaatcaa ataaaaagag gaataaacat gaaaatacga ataaaaggtc 900
caaacaaaga gacaataaac agagaggtat caattttgag acacagttat caaaaagaaa 960
tccaggccaa agaaacaatg aaggaagtac tctctgacaa catggaggta ttgagtgacc 1020
acataataat tgaggggctt tctgccgaag agataataaa aatgggtgaa acagttttgg 1080
agatagaaga attgcattaa attcaatttt actgtatttc ttactatgca tttaagcaaa 1140
ttgtaatcaa tgtcagcaaa taaactggaa aaagtgcgtt gtttctact 1189

<210> SEQ ID NO 5
<211> LENGTH: 1190
<212> TYPE: DNA
<213> ORGANISM: Influenza B virus

<400> SEQUENCE: 5
agcagaagca cgcactttct taaaatgtcg ctgtttggag acacaattgc ctacctgctt 60
tcattgacag aagatggaga aggcaaagca gaactagcag aaaaattaca ctgttggttc 120
ggtgggaaag aatttgacct agactctgcc ttggaatgga taaaaaacaa aagatgctta 180
actgatatac agaaagcact aattggtgcc tctatctgct ttttaaaacc caaagaccag 240
gaaagaaaaa gaagattcat cacagagccc ctatcaggaa tgggaacaac agcaacaaaa 300
aagaagggcc tgattctagc tgagagaaaa atgagaaaat gtgtgagctt ccatgaagca 360
tttgaaatag cagaaggcca tgaaagctca gcgttactat attgtctcat ggtcatgtac 420
ctgaatcctg gaaattattc aatgcaagta aaactaggaa cgctctgtgc tttgtgcgaa 480
aaacaagcat cacattcaca cagggctcat agcagagcag cgagatcttc agtgcccgga 540
gtgagacggg aaatgcagat ggtctcagct atgaacacag caaaaacaat gaatggaatg 600

-continued

```
ggaaaaggag aagacgtcca aaaactggca gaagaactgc aaagcaacat tggagtattg    660

agatctcttg gggcaagtca aaagaatggg gaaggaattg caaaggatgt aatggaagtg    720

ctaaagcaga gctctatggg aaattcagct cttgtgaaga aatacctata atgctcgaac    780

catttcagat tctttcaatt tgttctttta ttttatcagc tctccatttc atggcttgga    840

caataggaca tttaaatcaa ataaaaagag gagtaaacat gaaaatacga ataaaggggc    900

caaataaaga gacaataaac agagaggtat caattttgag acacagttac caaaaagaaa    960

tccaggctaa agaagcaatg aaggaagtac tctctgacaa catggaggta ttgagtgacc   1020

acatagtaat tgaggggctt tctgctgaag agataataaa aatgggtgaa acagttttgg   1080

aggtagaaga atttcattaa attcaatttt tactgtactt cttactatgc atttaagcaa   1140

attgtaatca atgtcagcaa ataaactgga aaaagtgcgt tgtttctact              1190
```

```
<210> SEQ ID NO 6
<211> LENGTH: 1190
<212> TYPE: DNA
<213> ORGANISM: Influenza B virus

<400> SEQUENCE: 6

agcagaagca cgcactttct taaaatgtcg ctgtttggag acacaattgc ctacctgctt     60

tcattgacag aagatggaga aggcaaagca gaactagcag aaaaattaca ctgttggttc    120

ggtgggaaag aatttgacct agactctgcc ttggaatgga taaaaaacaa aagatgctta    180

actgatatac agaaagcact aattggtgcc tctatctgct tttaaaaacc caaagaccag    240

gaaagaaaaa gaagattcat cacagagccc ctatcaggag tgggaacaac agcaacaaaa    300

aagaagggcc tgattctagc tgagagaaaa atgagaaaat gtgtgagctt ccatgaagca    360

tttgaaatag cagaaggcca tgaaagctca gcgttactat attgtctcat ggtcatgtac    420

ctgaatcctg gaaattattc aatgcaagta aaactaggaa cgctctgtgc tttgtgcgaa    480

aaacaagcat cacattcaca cagggctcat agcagagcag cgagatcttc agtgcccgga    540

gtgagacggg aaatgcagat ggtctcagct atgaacacag caaaaacaat gaatggaatg    600

ggaaaaggag aagacgtcca aaaactggca gaagaactgc aaagcaacat tggagtattg    660

agatctcttg gggcaagtca aaagaatggg gaaggaattg caaaggatgt aatggaagtg    720

ctaaagcaga gctctatggg aaattcagct cttgtgaaga aatacctata atgctcgaac    780

catttcagat tctttcaatt tgttctttta ttttatcagc tctccatttc atggcttgga    840

caataggaca tttaaatcaa ataaaaagag gagtaaacat gaaaatacga ataaaggggc    900

caaataaaga gacaataaac agagaggtat caattttgag acacagttac caaaaagaaa    960

tccaggctaa agaagcaatg aaggaagtac tctctgacaa catggaggta ttgagtgacc   1020

acatagtaat tgaggggctt tctgctgaag agataataaa aatgggtgaa acagttttgg   1080

aggtagaaga atttcattaa attcaatttt tactgtactt cttactatgc atttaagcaa   1140

attgtaatca atgtcagcaa ataaactgga aaaagtgcgt tgtttctact              1190
```

```
<210> SEQ ID NO 7
<211> LENGTH: 1189
<212> TYPE: DNA
<213> ORGANISM: Influenza B virus

<400> SEQUENCE: 7

agcagaagca cgcactttct taaaatgtcg ctgtttggag acacaattgc ctacctgctt     60

tcattgacag aagatggaga aggcaaagca gaactagcag aaaaattaca ctgttggttt    120
```

-continued ggtgggaaag aatttgacct agactctgcc ttggaatgga taaaaaacaa aagatgctta 180
actgatatac aaaaagcact aattggtgcc tctatatgct ttttaaaacc caaagaccag 240
gaaagaaaaa gaagattcat cacagagccc ttatcaggaa tgggaacaac agcaacaaaa 300
aagaaaggcc tgattctggc tgagagaaaa atgagaagat gtgtgagctt tcatgaagca 360
tttgaaatag cagaaggcca tgaaagctca gcgctactat actgtctcat ggtcatgtac 420
ctgaatcctg gaaattattc aatgcaagta aaactaggaa cgctctgtgc tttatgcgag 480
aaacaagcat cacattcaca cagggctcat agcagagcag cgagatcttc agtgcctgga 540
gtgagacgag aaatgcagat ggtctcagct atgaacacag caaaaacaat gaatggaatg 600
ggaaaaggag aagacgtcca aaagttggca gaagagctgc aaagcaacat tggagtgctg 660
agatctcttg ggcaagtcca aaagaatggg gaagggattg caaaggatgt aatggaagtg 720
ctaaagcaga gctccatggg aaattcagct cttgtgaaga aatatctata atgctcgaac 780
catttcagat tctttcaatt tgttctttta tcttatcagc tctccatttc atggcttgga 840
caatagggca tttgaatcaa ataaaaagag gaataaacat gaaaatacga ataaaaggtc 900
caaacaaaga gacaataaac agagaggtat caattttgag acacagttat caaaaagaaa 960
tccaggccaa agaaacaatg aaggaagtac tctctgacaa catggaggta ttgagtgacc 1020
acataataat tgaggggctt tctgccgaag agataataaa aatgggtgaa acagttttgg 1080
agatagaaga attgcattaa attcaatttt actgtatttc ttactatgca tttaagcaaa 1140
ttgtaatcaa tgtcagcaaa taaactggaa aaagtgcgtt gtttctact 1189

<210> SEQ ID NO 8
<211> LENGTH: 558
<212> TYPE: DNA
<213> ORGANISM: Influenza B virus

<400> SEQUENCE: 8
agcagaagca gaggatttgt ttagtcactg gcaaacagga aaaaatggcg aacaacatga 60
ccacaacaca aattgaggtg ggtccgtgat gacccaatgg atacaagtcc ttatcaactc 120
tgcatagatt gaatgcatat gaccagagtg gaaggcttgt tgctaaactt gttgccactg 180
atgatcttac agtggaggat gaagaagatg gccatcggat cctcaactca ctcttcgagc 240
gtcttaatga aggacattca aagccaattc gagcagctga aactgcggtg ggagtcttat 300
cccaatttgg tcaagagcac cgattatcac cagaagaggg agacaattag actggtcacg 360
gaagaacttt atcttttaag taaaagaatt gatgataaca tattattcca caaaacagta 420
atagctaaca gctccataat agctgacatg gttgtatcat tatcattatt agaaacattg 480
tatgaaatga aggatgtggt tgaagtgtac agcaggcagt gcttgtgaat ttaaaataaa 540
aatcctcttg ttactact 558

<210> SEQ ID NO 9
<211> LENGTH: 630
<212> TYPE: DNA
<213> ORGANISM: Influenza B virus

<400> SEQUENCE: 9
agcagaagca gaggatttgt ttagtcactg gcaaacagga aaaaatggcg aacaacatga 60
ccacaacaca aattgaggtg ggtccgggag caaccaatgc caccataaac tttgaagcag 120
gaattctgga gtgctatgaa aggctttcat ggcaaagatg atgacccaat ggatacaagt 180
ccttatcaac tctgcataga ttgaatgcat atgaccagag tggaaggctt gttgctaaac 240

-continued

```
ttgttgccac tgatgatctt acagtggagg atgaagaaga tggccatcgg atcctcaact    300

cactcttcga gcgtcttaat gaaggacatt caaagccaat tcgagcagct gaaactgcgg    360

tgggagtctt atcccaattt ggtcaagagc accgattatc accagaagag ggagacaatt    420

agactggtca cggaagaact ttatctttta agtaaaagaa ttgatgataa catattattc    480

cacaaaacag taatagctaa cagctccata atagctgaca tggttgtatc attatcatta    540

ttagaaacat tgtatgaaat gaaggatgtg gttgaagtgt acagcaggca gtgcttgtga    600

atttaaaata aaaatcctct tgttactact                                      630
```

<210> SEQ ID NO 10
<211> LENGTH: 687
<212> TYPE: DNA
<213> ORGANISM: Influenza B virus

<400> SEQUENCE: 10

```
agcagaagca gaggatttgt ttagtcactg gcaaacagga aaaaatggcg aacaacatga     60

ccacaacaca aattgaggtg ggtccgggag caaccaatgc caccataaac tttgaagcag    120

gaattctgga gtgctatgaa aggctttcat ggcaaagagc ccttgactac cctggtcaag    180

accgcctaaa cagactaaag agaaaattag agtcatgatg acccaatgga tacaagtcct    240

tatcaactct gcatagattg aatgcatatg accagagtgg aaggcttgtt gctaaacttg    300

ttgccactga tgatcttaca gtggaggatg aagaagatgg ccatcggatc ctcaactcac    360

tcttcgagcg tcttaatgaa ggacattcaa agccaattcg agcagctgaa actgcggtgg    420

gagtcttatc ccaatttggt caagagcacc gattatcacc agaagaggga gacaattaga    480

ctggtcacgg aagaacttta tcttttaagt aaaagaattg atgataacat attattccac    540

aaaacagtaa tagctaacag ctccataata gctgacatgg ttgtatcatt atcattatta    600

gaaacattgt atgaaatgaa ggatgtggtt gaagtgtaca gcaggcagtg cttgtgaatt    660

taaaataaaa atcctcttgt tactact                                         687
```

<210> SEQ ID NO 11
<211> LENGTH: 708
<212> TYPE: DNA
<213> ORGANISM: Influenza B virus

<400> SEQUENCE: 11

```
agcagaagca gaggatttgt ttagtcactg gcaaacagga aaaaatggcg aacaacatga     60

ccacaacaca aattgaggtg ggtccgggag caaccaatgc caccataaac tttgaagcag    120

gaattctgga gtgctatgaa aggctttcat ggcaaagagc ccttgactac cctggtcaag    180

accgcctaaa cagactaaag agaaaattag agtcaagaat aaagactcac aacaaatgat    240

gacccaatgg atacaagtcc ttatcaactc tgcatagatt gaatgcatat gaccagagtg    300

gaaggcttgt tgctaaactt gttgccactg atgatcttac agtggaggat gaagaagatg    360

gccatcggat cctcaactca ctcttcgagc gtcttaatga aggacattca aagccaattc    420

gagcagctga aactgcggtg ggagtcttat cccaatttgg tcaagagcac cgattatcac    480

cagaagaggg agacaattag actggtcacg gaagaacttt atcttttaag taaaagaatt    540

gatgataaca tattattcca caaaacagta atagctaaca gctccataat agctgacatg    600

gttgtatcat tatcattatt agaaacattg tatgaaatga aggatgtggt tgaagtgtac    660

agcaggcagt gcttgtgaat ttaaaataaa aatcctcttg ttactact                 708
```

<210> SEQ ID NO 12

<211> LENGTH: 756
<212> TYPE: DNA
<213> ORGANISM: Influenza B virus

<400> SEQUENCE: 12

```
agcagaagca gaggatttgt ttagtcactg gcaaacagga aaaaatggcg aacaacatga     60

ccacaacaca aattgaggtg ggtccgggag caaccaatgc caccataaac tttgaagcag    120

gaattctgga gtgctatgaa aggctttcat ggcaaagagc ccttgactac cctggtcaag    180

accgcctaaa cagactaaag agaaaattag agtcaagaat aaagactcac aacaaaagtg    240

agcctgaaag taaaaggatg tcccttgaag agagaaaagc aatttgatga cccaatggat    300

acaagtcctt atcaactctg catagattga atgcatatga ccagagtgga aggcttgttg    360

ctaaacttgt tgccactgat gatcttacag tggaggatga agaagatggc catcggatcc    420

tcaactcact cttcgagcgt cttaatgaag gacattcaaa gccaattcga gcagctgaaa    480

ctgcggtggg agtcttatcc caatttggtc aagagcaccg attatcacca gaagagggag    540

acaattagac tggtcacgga agaactttat cttttaagta aaagaattga tgataacata    600

ttattccaca aaacagtaat agctaacagc tccataatag ctgacatggt tgtatcatta    660

tcattattag aaacattgta tgaaatgaag gatgtggttg aagtgtacag caggcagtgc    720

ttgtgaattt aaaataaaaa tcctcttgtt actact                              756
```

<210> SEQ ID NO 13
<211> LENGTH: 443
<212> TYPE: DNA
<213> ORGANISM: Influenza B virus

<400> SEQUENCE: 13

```
agcagaagca gaggatttgt ttagtcactg gcaaacagga aaaaatggcg aacaacatga     60

ccacaacaca aattgagtgg aggatgaaga agatggccat cggatcctca actcactctt    120

cgagcgtctt aatgaaggac attcaaagcc aattcgagca gctgaaactg cggtgggagt    180

cttatcccaa tttggtcaag agcaccgatt atcaccagaa gagggagaca attagactgg    240

tcacggaaga actttatctt ttaagtaaaa gaattgatga taacatatta ttccacaaaa    300

cagtaatagc taacagctcc ataatagctg acatggttgt atcattatca ttattagaaa    360

cattgtatga aatgaaggat gtggttgaag tgtacagcag gcagtgcttg tgaatttaaa    420

ataaaaatcc tcttgttact act                                            443
```

<210> SEQ ID NO 14
<211> LENGTH: 442
<212> TYPE: DNA
<213> ORGANISM: Influenza B virus

<400> SEQUENCE: 14

```
agcagaagca gaggatttgt ttagtcactg gcaaacagga aaaatggcgg acaatatgac     60

cacaacacaa attgagtgga ggatgaagaa gatggccatc ggatcctcaa ttcactcttc    120

gagcgtctta atgaaggaca ttcaaagcca attcgagcag ctgaaactgc ggtgggagtc    180

ttatcccaat ttggtcaaga gcaccgatta tcaccagaag agggagacaa ttagactggt    240

cacggaagaa ctttatcttt taagtaaaag aattgatgat aacatattgt tccacaaaac    300

agtaatagct aacagctcca taatagctga catggttgta tcattatcat tattagaaac    360

attgtatgaa atgaaggatg tggttgaagt gtacagcagg cagtgcttgt gaatttaaaa    420

taaaaatcct cttgttacta ct                                             442
```

<210> SEQ ID NO 15
<211> LENGTH: 1023
<212> TYPE: DNA
<213> ORGANISM: Influenza B virus

<400> SEQUENCE: 15

```
agcagaagca gaggatttgt ttagtcactg gcaaacagga aaaaatggcg aacaacatga      60
ccacaacaca aattgaggtg ggtccgggag caaccaatgc caccataaac tttgaagcag     120
gaattctgga gtgctatgaa aggctttcat ggcaaagata atgtacagga tgcaactcct     180
gtcttgcatt gcactaagtc ttgcacttgt cacaaacagt gcacctactt cttcgtcgac     240
aaagaaaaca cagctacaac tggagcattt actgctggat ttacagatga ttttgaatgg     300
aattaataat tacaagaatc ccaaactcac caggatgctc acatttaagt tttacatgcc     360
caagaaggcc acagaactga aacatcttca gtgtctagaa gaagaactca aacctctgga     420
ggaagtgcta aatttagctc aaagcaaaaa ctttcactta agacccaggg acttaatcag     480
caatatcaac gtaatagttc tggaactaaa gggatctgaa acaacattca tgtgtgaata     540
tgctgatgag acagcaacca ttgtagaatt tctgaacaga tggattacct tttgtcaaag     600
catcatctca acactaactt gataatacta accttcttct ctttcttctc ctgacagtgg     660
aggatgaaga agatggccat cggatcctca actcactctt cgagcgtctt aatgaaggac     720
attcaaagcc aattcgagca gctgaaactg cggtgggagt cttatcccaa tttggtcaag     780
agcaccgatt atcaccagaa gagggagaca attagactgg tcacggaaga actttatctt     840
ttaagtaaaa gaattgatga taacatatta ttccacaaaa cagtaatagc taacagctcc     900
ataatagctg acatggttgt atcattatca ttattagaaa cattgtatga aatgaaggat     960
gtggttgaag tgtacagcag gcagtgcttg tgaatttaaa ataaaaatcc tcttgttact    1020
act                                                                  1023
```

<210> SEQ ID NO 16
<211> LENGTH: 1149
<212> TYPE: DNA
<213> ORGANISM: Influenza B virus

<400> SEQUENCE: 16

```
agcagaagca gaggatttgt ttagtcactg gcaaacagga aaaaatggcg aacaacatga      60
ccacaacaca aattgaggtg ggtccgggag caaccaatgc caccataaac tttgaagcag     120
gaattctgga gtgctatgaa aggctttcat ggcaaagagc ccttgactac cctggtcaag     180
accgcctaaa cagactaaag agaaaattag agtcaagaat aaagactcac aacaaaagtg     240
agcctgaaag taaaaggatg tcccttgaag agagaaaagc aatttaatgt acaggatgca     300
actcctgtct tgcattgcac taagtcttgc acttgtcaca aacagtgcac ctacttcttc     360
gtcgacaaag aaaacacagc tacaactgga gcatttactg ctggatttac agatgatttt     420
gaatggaatt aataattaca agaatcccaa actcaccagg atgctcacat ttaagtttta     480
catgcccaag aaggccacag aactgaaaca tcttcagtgt ctagaagaag aactcaaacc     540
tctggaggaa gtgctaaatt tagctcaaag caaaaacttt cacttaagac ccagggactt     600
aatcagcaat atcaacgtaa tagttctgga actaaaggga tctgaaacaa cattcatgtg     660
tgaatatgct gatgagacag caaccattgt agaatttctg aacagatgga ttaccttttg     720
tcaaagcatc atctcaacac taacttgata atactaacct tcttctcttt cttctcctga     780
cagtggagga tgaagaagat ggccatcgga tcctcaactc actcttcgag cgtcttaatg     840
```

-continued

```
aaggacattc aaagccaatt cgagcagctg aaactgcggt gggagtctta tcccaatttg    900

gtcaagagca ccgattatca ccagaagagg gagacaatta gactggtcac ggaagaactt    960

tatcttttaa gtaaaagaat tgatgataac atattattcc acaaaacagt aatagctaac   1020

agctccataa tagctgacat ggttgtatca ttatcattat tagaaacatt gtatgaaatg   1080

aaggatgtgg ttgaagtgta cagcaggcag tgcttgtgaa tttaaaataa aaatcctctt   1140

gttactact                                                           1149
```

<210> SEQ ID NO 17
<211> LENGTH: 1221
<212> TYPE: DNA
<213> ORGANISM: Influenza B virus

<400> SEQUENCE: 17

```
agcagaagca gaggatttgt ttagtcactg gcaaacagga aaaaatggcg aacaacatga     60

ccacaacaca aattgaggtg ggtccgggag caaccaatgc caccataaac tttgaagcag    120

gaattctgga gtgctatgaa aggctttcat ggcaaagagc ccttgactac cctggtcaag    180

accgcctaaa cagactaaag agaaaattag agtcaagaat aaagactcac aacaaaagtg    240

agcctgaaag taaaaggatg tcccttgaag agagaaaagc aattggagta aaaatgatga    300

aagtactcct atttatgaat ccgtctgctg gaattgaagg gtttgagcca tactgttaat    360

gtacaggatg caactcctgt cttgcattgc actaagtctt gcacttgtca caaacagtgc    420

acctacttct tcgtcgacaa agaaaacaca gctacaactg gagcatttac tgctggattt    480

acagatgatt ttgaatggaa ttaataatta caagaatccc aaactcacca ggatgctcac    540

atttaagttt tacatgccca agaaggccac agaactgaaa catcttcagt gtctagaaga    600

agaactcaaa cctctggagg aagtgctaaa tttagctcaa agcaaaaact ttcacttaag    660

acccagggac ttaatcagca atatcaacgt aatagttctg gaactaaagg gatctgaaac    720

aacattcatg tgtgaatatg ctgatgagac agcaaccatt gtagaatttc tgaacagatg    780

gattaccttt tgtcaaagca tcatctcaac actaacttga taatactaac cttcttctct    840

ttcttctcct gacagtggag gatgaagaag atggccatcg gatcctcaac tcactcttcg    900

agcgtcttaa tgaaggacat tcaaagccaa ttcgagcagc tgaaactgcg gtgggagtct    960

tatcccaatt tggtcaagag caccgattat caccagaaga gggagacaat tagactggtc   1020

acggaagaac tttatctttt aagtaaaaga attgatgata acatattatt ccacaaaaca   1080

gtaatagcta acagctccat aatagctgac atggttgtat cattatcatt attagaaaca   1140

ttgtatgaaa tgaaggatgt ggttgaagtg tacagcaggc agtgcttgtg aatttaaaat   1200

aaaaatcctc ttgttactac t                                             1221
```

<210> SEQ ID NO 18
<211> LENGTH: 1344
<212> TYPE: DNA
<213> ORGANISM: Influenza B virus

<400> SEQUENCE: 18

```
agcagaagca gaggatttgt ttagtcactg gcaaacagga aaaaatggcg aacaacatga     60

ccacaacaca aattgaggtg ggtccgggag caaccaatgc caccataaac tttgaagcag    120

gaattctgga gtgctatgaa aggctttcat ggcaaagagc ccttgactac cctggtcaag    180

accgcctaaa cagactaaag agaaaattag agtcaagaat aaagactcac aacaaaagtg    240

agcctgaaag taaaaggatg tcccttgaag agagaaaagc aattggagta aaaatgatga    300
```

-continued

```
aagtactcct atttatgaat ccgtctgctg gaattgaagg gtttgagcca tactgtatga    360

aaagttcctc aaatagcaac tgtacgaaat acaattggac cgattaccct tcaacaccag    420

ggaggtgcct tgatgacata gaagaagaac cagaggatgt tgatggccca actgaaatat    480

aatgtacagg atgcaactcc tgtcttgcat tgcactaagt cttgcacttg tcacaaacag    540

tgcacctact tcttcgtcga caaagaaaac acagctacaa ctggagcatt tactgctgga    600

tttacagatg attttgaatg gaattaataa ttacaagaat cccaaactca ccaggatgct    660

cacatttaag ttttacatgc ccaagaaggc cacagaactg aaacatcttc agtgtctaga    720

agaagaactc aaacctctgg aggaagtgct aaatttagct caaagcaaaa actttcactt    780

aagacccagg gacttaatca gcaatatcaa cgtaatagtt ctggaactaa agggatctga    840

aacaacattc atgtgtgaat atgctgatga gacagcaacc attgtagaat ttctgaacag    900

atggattacc ttttgtcaaa gcatcatctc aacactaact tgataatact aaccttcttc    960

tctttcttct cctgacagtg gaggatgaag aagatggcca tcggatcctc aactcactct   1020

tcgagcgtct taatgaagga cattcaaagc caattcgagc agctgaaact gcggtgggag   1080

tcttatccca atttggtcaa gagcaccgat tatcaccaga agagggagac aattagactg   1140

gtcacggaag aactttatct tttaagtaaa agaattgatg ataacatatt attccacaaa   1200

acagtaatag ctaacagctc cataatagct gacatggttg tatcattatc attattagaa   1260

acattgtatg aaatgaagga tgtggttgaa gtgtacagca ggcagtgctt gtgaatttaa   1320

aataaaaatc ctcttgttac tact                                          1344
```

<210> SEQ ID NO 19
<211> LENGTH: 56
<212> TYPE: PRT
<213> ORGANISM: Influenza B virus

<400> SEQUENCE: 19

```
Gly Ala Ser Ile Cys Phe Leu Lys Pro Lys Asp Gln Glu Arg Lys Arg
1               5                   10                  15

Arg Phe Ile Thr Glu Pro Leu Ser Gly Met Gly Thr Thr Ala Thr Lys
            20                  25                  30

Lys Lys Gly Leu Ile Leu Ala Glu Arg Lys Met Arg Arg Cys Val Ser
        35                  40                  45

Phe His Glu Ala Phe Glu Ile Ala
    50                  55
```

<210> SEQ ID NO 20
<211> LENGTH: 56
<212> TYPE: PRT
<213> ORGANISM: Influenza B virus

<400> SEQUENCE: 20

```
Gly Ala Ser Ile Cys Phe Leu Lys Pro Lys Asp Gln Glu Arg Lys Arg
1               5                   10                  15

Arg Phe Ile Thr Glu Pro Leu Ser Gly Val Gly Thr Thr Ala Thr Lys
            20                  25                  30

Lys Lys Gly Leu Ile Leu Ala Glu Arg Lys Met Arg Arg Cys Val Ser
        35                  40                  45

Phe His Glu Ala Phe Glu Ile Ala
    50                  55
```